(12) United States Patent
Reese

(10) Patent No.: US 6,711,460 B1
(45) Date of Patent: Mar. 23, 2004

(54) PHARMACEUTICAL SYSTEM IN WHICH PHARMACEUTICAL CARE IS PROVIDED BY A REMOTE PROFESSIONAL SERVING MULTIPLE PHARMACIES

(75) Inventor: Rod Reese, New Philadelphia, OH (US)

(73) Assignee: Diebold Incorporated, North Canton, OH (US)

( * ) Notice: Subject to any disclaimer, the term of this patent is extended or adjusted under 35 U.S.C. 154(b) by 0 days.

(21) Appl. No.: 10/172,391

(22) Filed: Jun. 14, 2002

Related U.S. Application Data

(60) Provisional application No. 60/299,116, filed on Jun. 18, 2001.

(51) Int. Cl.[7] .............................. G06F 7/00; G06F 17/00
(52) U.S. Cl. ........................ 700/216; 700/237; 700/244
(58) Field of Search ................................. 700/216, 231, 700/232, 237, 241, 244

(56) References Cited

U.S. PATENT DOCUMENTS

| | | | | |
|---|---|---|---|---|
| 5,502,944 A | * | 4/1996 | Kraft et al. ................. | 700/236 |
| 5,797,515 A | * | 8/1998 | Liff et al. ................... | 700/241 |
| 5,907,493 A | * | 5/1999 | Boyer et al. ................ | 700/231 |
| 6,202,004 B1 | * | 3/2001 | Valerino, Sr. ............... | 700/218 |
| 6,330,491 B1 | * | 12/2001 | Lion ........................... | 700/237 |
| RE37,829 E | * | 9/2002 | Charhut et al. ............. | 700/216 |

* cited by examiner

*Primary Examiner*—Gene O Crawford
(74) *Attorney, Agent, or Firm*—Ralph E. Jocke; Daniel D. Wasil; Walker & Jocke

(57) ABSTRACT

A pharmaceutical system and method of operation in which a single remote professional provides pharmaceutical care and oversight of multiple local pharmacies. A control location is connected through an electronic network to one or more individual pharmacies, each of which may be located at a different physical site. Each individual pharmacy includes one or more drug preparation areas, and one or more self-service or staffed customer terminals. A drug preparation area includes a robot, which is adapted to prepare prescriptions or other items, and which is connected by a pneumatic delivery system to one or more customer terminals within the pharmacy.

33 Claims, 14 Drawing Sheets

PHARMACEUTICAL SYSTEM IN WHICH PHARMACEUTICAL CARE IS PROVIDED BY A REMOTE PROFESSIONAL SERVING MULTIPLE PHARMACIES

This Application claims priority under 35 U.S.C. § 119(e) of Provisional Application No. 60/299,116 filed Jun. 18, 2001.

TECHNICAL FIELD

This invention relates to the delivery of outpatient care. Specifically this invention relates to a system and method for the automated preparation and delivery of prescription medications or other controlled substances to outpatients, and to the delivery of personalized care by a single pharmacist or other professional to outpatients in multiple pharmacies.

BACKGROUND ART

Providing medical care to patients on an outpatient basis customarily includes the delivery of medications. It may also involve delivering controlled items, such as syringes or orthopedic aids, for example, to individuals. While these things may be provided directly by the physician, they are more typically provided by issuing a prescription to the patient. The patient then takes the prescription to a pharmacist who provides the patient with the item described in the prescription. In connection with delivering those items to the patient, the pharmacist typically offers to provide counseling to the patient as to the expected use, side effects, or drug interactions.

In addition, outpatients may also need to obtain non-prescription items which are kept in the pharmacy. One example of such an item is a cough medication containing a small amount of narcotics which must be kept in the pharmacy, so that the sale of these items can be monitored.

In a traditional arrangement, a pharmacist is generally in charge of operating a single pharmacy, either alone or in concert with other pharmacists who are responsible to the lead pharmacist. Each pharmacy generally operates as a self-contained unit, with the pharmacist in each store responsible for maintaining patient records and for assembling medications or other items for those patients. As technology has advanced there have been improvements in the methods of preparing prescriptions, including automating counting, record keeping, and similar functions. In addition, with the advent of chain pharmacies, some previously isolated records may now be merged so that an individual store, which is part of a larger commonly owned or other related group of pharmacies, has access to patient records for patients who have purchased prescription medications or other items in any of the pharmacies that are a part of the group.

Pharmacies are also increasingly located within general merchandise stores. These general merchandise stores are often open during hours when traditional pharmacies are not open. Law, or industry practice, generally requires the presence of a pharmacist any time medications are being assembled or dispensed. In order to meet customer demand for pharmaceutical services during non-traditional hours, particularly in pharmacies incorporated in stores which are open extended hours, pharmacies have hired more pharmacists than would normally be required to run a single pharmacy. Because of this, in part, the need for trained pharmacists has increased, and there is currently a critical shortage of trained pharmacists.

In contrast, increased automation of services has decreased the time it takes to fill a single prescription. In addition, the number of prescriptions being filled has not increased as dramatically as the number of hours pharmaceutical services are commonly available. Because of this, the services of individual pharmacists may not be fully utilized, even in the face of a critical shortage of trained pharmacists.

In addition to the downtime created by the increased working hours of pharmacists, without a corresponding increase in workload, a second staffing problem exists. Smaller stores, particularly those in less urban areas, are unable to compete with their massive counterparts to attract the limited number of pharmacists currently being trained. Pharmacists who might otherwise be working in small independent pharmacies are choosing to work in larger pharmacies, which can generally afford to offer higher salaries and better benefits. Unable to attract pharmacists, some of these smaller stores may be forced to stop furnishing outpatient pharmaceutical care to outpatients. This may leave individuals in some areas without adequate access to outpatient pharmaceutical services.

Thus there exists a need for a system and method for furnishing outpatient pharmaceutical services in which a single pharmacist or other professional can serve multiple pharmacies, which may be either a collection of independent pharmacies or several branches of the same pharmacy. There further exists a need for a system and method for furnishing outpatient pharmaceutical services to outpatients which uses automation and innovative technology to permit each pharmacist or other professional to serve a larger client base. There further exists a need for systems and methods that provide automated delivery of pharmaceutical services to outpatients which will permit a smaller isolated pharmacy to continue to provide pharmaceutical services without being forced to compete with larger pharmaceutical groups for the exclusive services of one of the limited number of trained pharmacists.

DISCLOSURE OF INVENTION

It is an object of an exemplary form of the present invention to provide a system and method for delivering outpatient pharmaceutical care in which a single pharmacist is responsible for providing care in multiple pharmacies.

It is a further object of an exemplary form of the present invention to provide a system and method for furnishing outpatient pharmaceutical care in which the pharmacist managing the care may do so from a location other than the pharmacy.

It is a further object of an exemplary form of the present invention to provide a system and method for furnishing outpatient pharmaceutical care in which a remote pharmacist directs one or more robots to prepare prescriptions or other controlled items locally, in secured locations.

It is a further object of an exemplary form of the present invention to provide a system and method for furnishing outpatient pharmaceutical care in which the patient may access care through a stand-alone terminal within a store.

It is a further object of an exemplary form of the present invention to provide a system and method for furnishing outpatient pharmaceutical care in which the patient may access care through a drive-through terminal on the exterior of a store.

It is a further object of an exemplary form of the present invention to provide a system and method for furnishing outpatient pharmaceutical care with more accuracy than a traditional system by using automated mandatory verification before delivering the medication or other item to the patient.

It is a further object of an exemplary form of the present invention to provide a system and method for furnishing outpatient pharmaceutical care which provides increased assurance that each patient will be offered patient counseling with each item dispensed.

It is a further object of an exemplary form of the present invention to provide a system and method for furnishing outpatient pharmaceutical care which results in more effective counseling of patients by using a larger or multiple database of patient information.

It is a further object of an exemplary form of the present invention to provide a system and method for pharmaceutical outpatient care which results in more effective counseling of patients by using a systematically generated list of concerns that specifically relate to an individual patient and/or the item prescribed.

Further objects of exemplary forms of the present invention will be made apparent in the following Best Modes for Carrying Out Invention and appended claims.

The foregoing objects are accomplished in an exemplary embodiment which permits a single pharmacist or other professional who can deliver prescription medications, who will be referred to herein as a "pharmacist," to simultaneously serve several individual pharmacies. In an exemplary embodiment a pharmacist will generally work at a location that is remote from most or all of the individual pharmacies being served. In order to accomplish this, the remote pharmacist will be in direct computer connection, over a network, with each of the individual pharmacies being served. Through this network, the pharmacist will be connected with user service stations, drug vaults, and a customer service computer located within each individual pharmacy. The connection will include CCTV connections to each of these locations within the individual pharmacies, permitting the pharmacist to observe a robot or other device preparing prescriptions in the drug retrieval vault and in the drug compounding vault, and to communicate directly with customers and local technicians.

In an exemplary embodiment, the pharmacist's computer is adapted to permit the pharmacist to control the robots in one or more drug vaults from a remote location. The remote pharmacist is in interactive communication with the robots in the individual pharmacies as the robots prepare the items that are to be dispensed to each customer.

In an exemplary embodiment of a pharmacy the remote pharmacist will have access to one or more processing and data storage devices containing individual patient histories for the group of pharmacies he or she serves, general information about the drugs which may be dispensed, the rules that apply to the various insurance plans accepted by each pharmacy, persons registered to prescribe medications, and the items stocked in each location. These data storage and processing devices may be in the same physical location as the remote pharmacist, or the pharmacist may be connected to these devices through one or more networks. The network used in an exemplary embodiment is separated from any external network by a pharmacist's computer which includes a firewall, or other means to prevent unauthorized access.

Each of the individual pharmacies served by a remote pharmacist is equipped with an automated drug preparation and compounding area, and may have one or more self-service customer terminals through which the patient can access pharmaceutical services. The individual pharmacies may also have a traditional customer service area, which is staffed by an individual. A computer in each local pharmacy controls and coordinates the network within that pharmacy. It includes a firewall or other means to prevent unauthorized access. Each of the individual pharmacies is connected to a remote pharmacist via a computer network system.

Customer terminals, if they are part of an embodiment of an individual pharmacy, may be walk-up terminals inside the store or drive-through terminals on the outside of the pharmacy. Customer terminals include a way for the patient to submit a prescription to be filled, to communicate with the pharmacist, to pay for the prescription, and to take delivery of the prescription. These functions may all be contained in a single customer terminal or split between two or more customer terminals. Some of the functions of a customer terminal will be performed using (1) dedicated input devices, such as a card reader, a prescription scanner, or a bar code reader; (2) dedicated output devices, such as printers adapted to print drug information sheets and receipts; and (3) interactive communication devices, such as Closed Circuit Television ("CCTV"), and intranet or internet connections. Most customer terminals will also include access to a pneumatic delivery system, which connects the parts of the local pharmacy so that objects can be sent between them.

An exemplary embodiment of the drug preparation area will generally include two vaults in which robots prepare the items requested. An exemplary embodiment of the first vault will include storage cells around the walls of the vault. These storage cells will contain the medications or medication components most commonly used in a particular pharmacy, and other items that must be dispensed through the pharmacy. Such an embodiment will also include a preparation area that includes various automated counting or measuring devices.

In the exemplary embodiment a relatively simple robot is located within the drug retrieval vault. The robot is adapted to perform one or more tasks necessary to prepare simple pharmaceutical orders. The robot is also adapted to perform one or more tasks necessary to deliver the raw ingredients for more complicated pharmaceutical orders to the drug compounding vault. Finally, the robot is adapted to package and deliver the prepared pharmaceutical order to the customer. Actions of the robot are directed by a pharmacist from a remote location.

In addition, an exemplary embodiment of a pharmacy using the system and method of this invention includes a drug compounding vault. This vault is used to prepare medications which cannot be delivered to the patient in the form in which they are stored in the pharmacy. The compounding performed may be minor, such as mixing water with a powder just before the medication is delivered to the patient. It may also be more complex, such as preparing an individualized medication from several ingredients.

An exemplary embodiment of a drug compounding vault includes the various devices that a pharmacist would need to compound drugs. The exemplary drug compounding vault is in direct connection with the drug preparation vault via a pneumatic delivery tube. An exemplary embodiment may also include a sophisticated medical robot, equipped with various sensor devices similar to those used in surgical robots.

An exemplary robot in an exemplary drug compounding vault is adapted to perform complex manipulations with raw ingredients, using traditional compounding tools, at the direction of a remote pharmacist. The robot is also adapted to retrieve ingredients sent to it by the robot in the drug retrieval vault and to return the compounded pharmaceutical item to the robot in the drug retrieval vault.

An exemplary embodiment of a pharmacy may also include a traditional customer service desk at which an individual may speak directly with a technician. In an exemplary embodiment of a system including this feature, the technician will gather the information from the patient, and transmit it to the remote pharmacist, using devices that may be similar to those available to the customer at a customer terminal. The look and feel of the interaction at a customer service desk will generally be similar to the look and feel of a traditional pharmacy interaction, with the exception that patients will receive counseling over the CCTV rather than face-to-face.

In addition, in an exemplary embodiment of a pharmacy using this method, a prescriber or a customer may use the telephone to request pharmaceutical care. Depending on the laws of the state, the technician at the service desk will either transmit the prescription in the form of an audio or digital recording to the remote pharmacist or will enter the information into the pharmacy computer which will then transmit it in facsimile form to the remote pharmacist. The system may also be configured to accept direct computer-to-computer transmissions of prescriptions from individual prescribers.

BEST MODES FOR CARRYING OUT INVENTION

The Exemplary Pharmaceutical System

Figure 1:
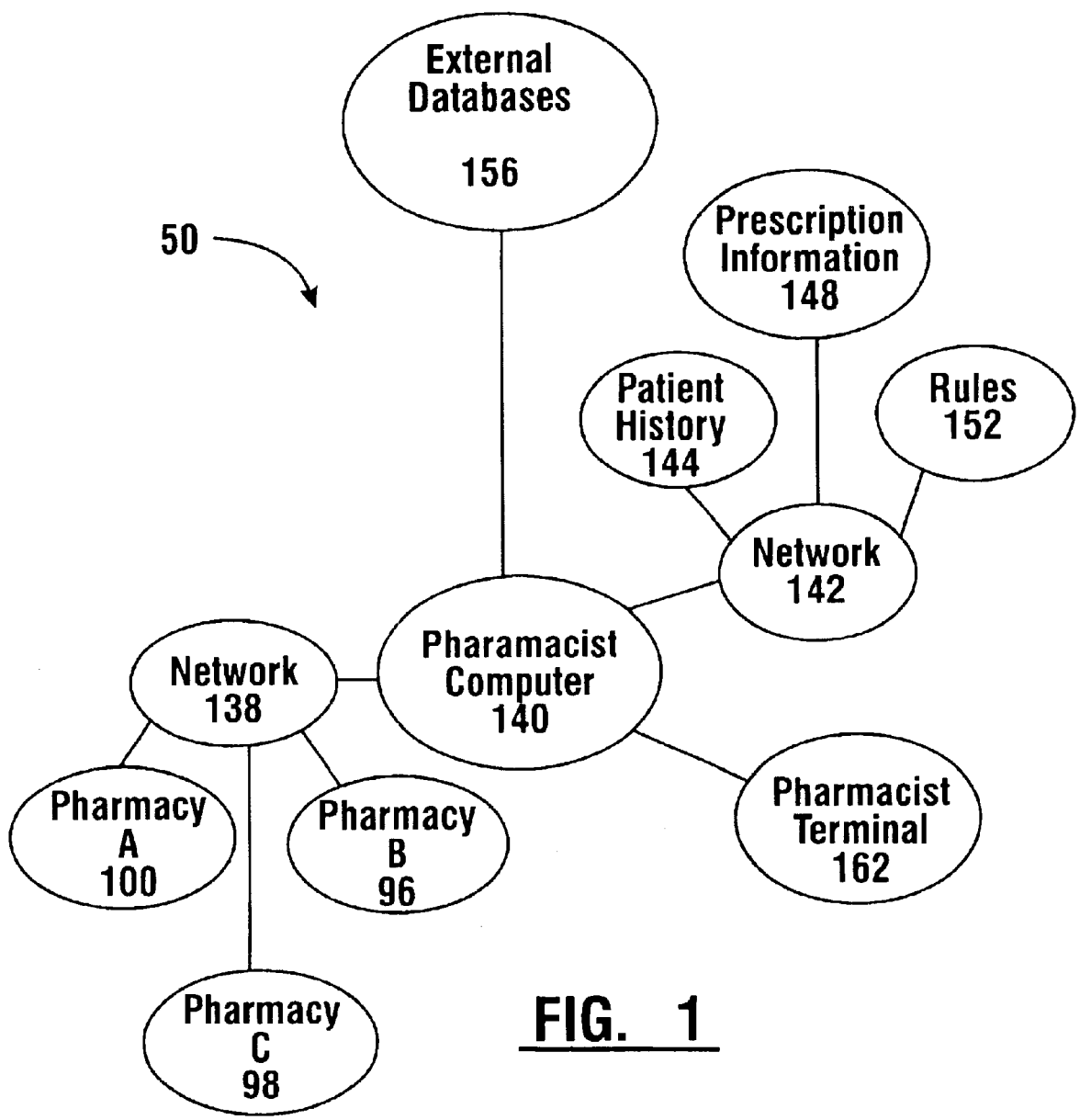
FIG. 1 is a schematic representation an exemplary pharmaceutical system.

Referring now to the drawings and particularly to FIG. 1, there is shown therein a schematic representation of an exemplary embodiment of a pharmaceutical system, generally designated by reference numeral 50. The pharmaceutical system 50 comprises a remote pharmacist computer 140, operatively linked over a network 138 to several individual pharmacies 96–100. In addition, the remote pharmacist computer may also be linked directly, or through one or more networks, to various databases which are represented schematically as external databases 156, patient history 144, prescription information 148, and rules 152.

Figure 2:
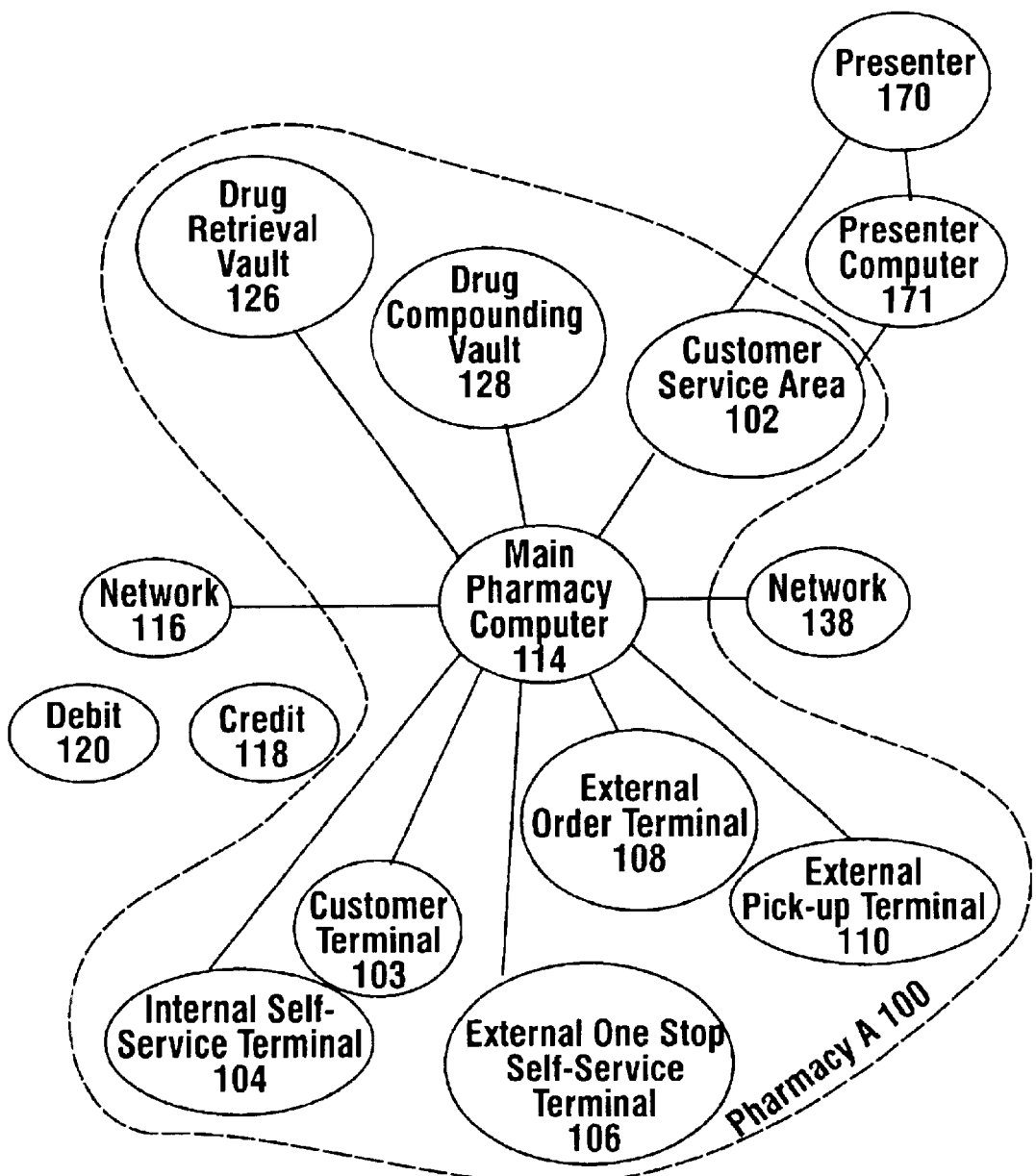
FIG. 2 is a schematic representation of an exemplary pharmacy.
Figure 3:
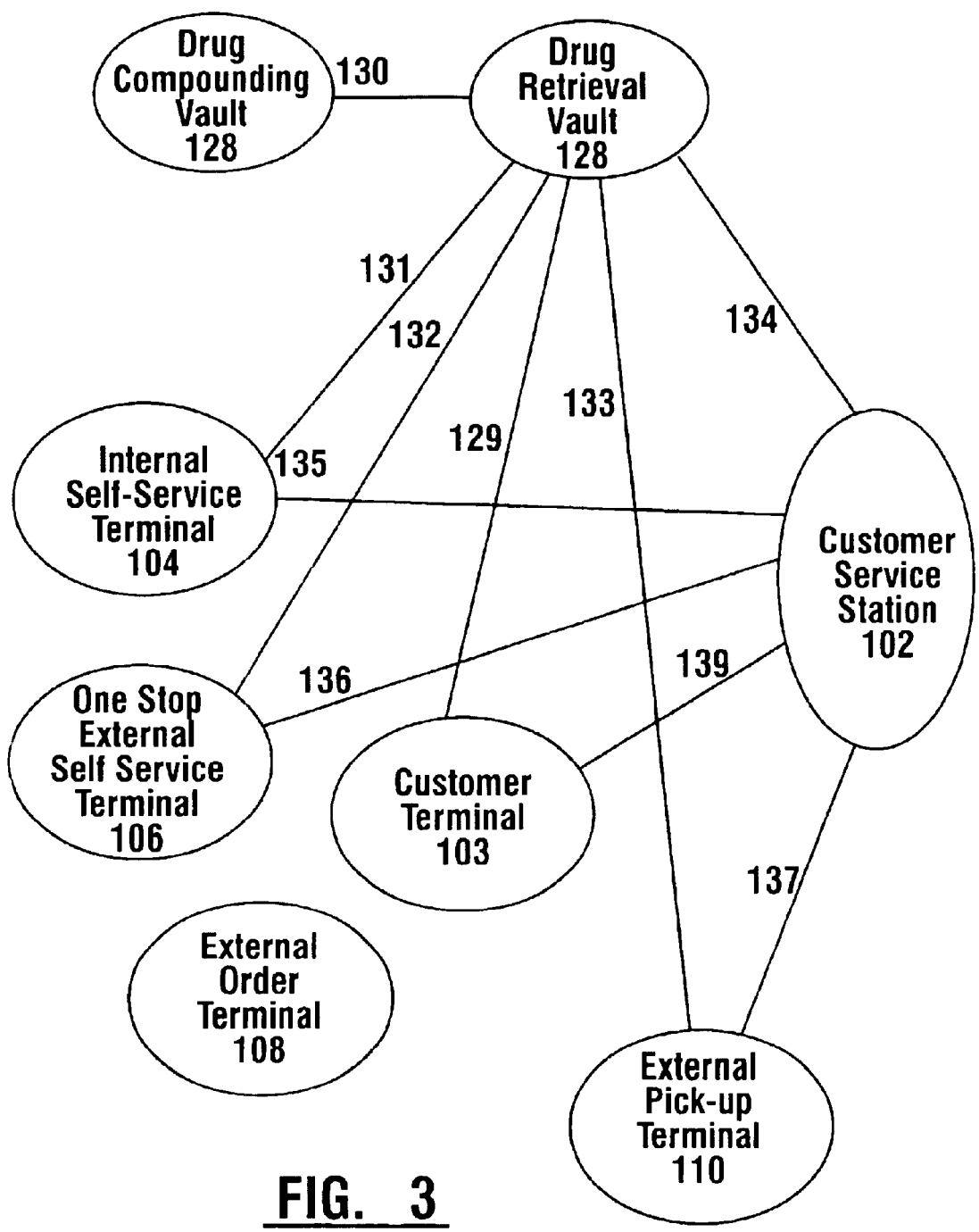
FIG. 3 is a schematic representation of the pneumatic delivery system connections.

A portion of the exemplary pharmaceutical system, an individual pharmacy, is illustrated in more detail in FIG. 2. The pharmacy is generally designated by reference numeral 100. Pharmacy 100 includes a customer service area 102, a drug retrieval vault 126, a drug compounding vault 128, and one or more customer terminals, such as an internal self-service terminal 104, a one-stop external self-service terminal 106, an external order terminal 108 or an external pickup terminal 110. A generic customer terminal 103 is illustrated in FIGS. 2 and 3, and should be understood to be interchangeable with any of the specialized terminals 104–110. Any reference herein to a customer terminal 103 should be understood to be a reference to any of the terminals 104–110. Any reference herein to customer terminals 103 should be understood to be a reference to any appropriate combination of terminals 104–110.

The exemplary pharmacy 100 also includes at least one pharmacy computer 114 electronically connected to and coordinating one or more customer terminals 104–110, customer service area 102, and the drug vaults 126 and 128, as illustrated in FIG. 2. The pharmacy computer 114 contains, or is directly linked to databases containing at least a linked list of local prescribers and identifying numbers, and a list of current prescriptions held by the pharmacy 100. In addition, the exemplary pharmacy computer 114 is connected with the remote pharmacist via a network 138.

In the exemplary embodiment, the drug retrieval vault 126 is physically connected with the drug compounding vault 128 by a pneumatic delivery tube 130, as schematically shown in FIG. 3. The drug retrieval vault 126 is also in physical connection with a customer terminal 103, an internal self-service terminal 104, a customer service area 102, a one-stop external self-service terminal 106, and an external pickup terminal 110 via pneumatic delivery tubes 129, 131, 134, 132 and 133. Although in this exemplary embodiment, the connection between a customer terminal 103 and the customer service area 102 or the drug retrieval vault 126 is direct, as can be seen in the schematic representation of the pneumatic delivery system in FIG. 3, in other embodiments the pneumatic delivery system may be configured as a web of interconnected pneumatic delivery tubes, with the customer, the remote pharmacist, or the technician controlling the transmission of items to one or more of a number of destinations. Exemplary embodiments may include pneumatic tube systems like that described in U.S. Pat. No. 6,146,057, the disclosure of which is incorporated herein by reference.

An exemplary embodiment includes one or more customer terminals 103 which permit a customer to order and receive pharmaceutical items without using the customer service area 102. The features of a particular customer terminal 103 may vary depending on a number of factors. For example, a drive-up terminal may incorporate different features than a terminal located within a store. Similarly, a customer terminal 103 that is intended to be a one-stop terminal may incorporate different features than one that is intended to accept an order for later pick-up at either a pick-up terminal or the customer service area 102. The general features that are likely to be included in an exemplary customer terminal 103 are described below.

Figure 4:
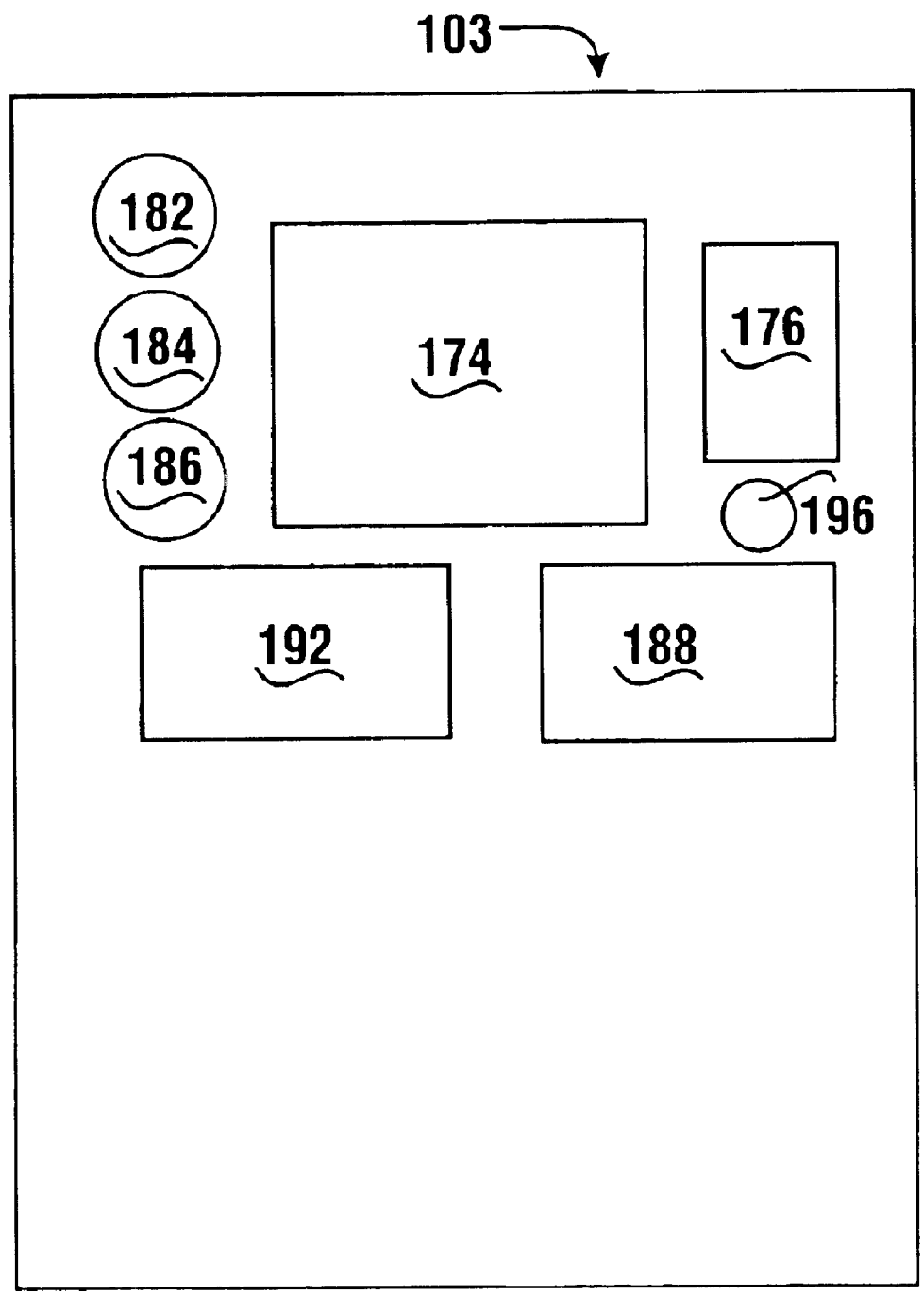
FIG. 4 is a front view of an exemplary customer terminal.

An exemplary embodiment of a customer terminal 103 is shown in more detail in FIG. 4. This exemplary embodiment of a customer terminal 103 includes a dual purpose video screen 174. The video screen 174 functions as part of a CCTV system which is in connection with a remote pharmacist. The CCTV may also be in connection with the customer service area 102. When functioning as a CCTV, the video screen 174 works in conjunction with the speaker 184, microphone 186, and CCTV camera 182 to permit interactive communication between the customer, the remote pharmacist, and the technician at the customer service area 102. It also serves as part of a computer system which permits the customer to interact with either the customer service area 102 or a remote pharmacist by using communication software, firmware, and electronic input devices such as a mouse, keyboard, keypad, or a touch screen.

The exemplary embodiment of a customer terminal 103 provides various ways to submit prescription or other order information, identified schematically as dedicated input devices 176. These dedicated input devices 176 may include, for example, a magnetic or other type of card reader, a prescription scanner, check scanner, keyboard, keypad, graffiti pad, microphone, and/or optical reader which is capable of reading bar or other information. The customer may also provide information using multipurpose devices such as a touch screen, CCTV camera, or wireless communication devices. Any method of accepting information from a customer in a format that may be transmitted from the pharmacy computer 114 to a remote location using electronic or wireless technology may be used. In other embodiments the customer terminal may include biometric reading devices such as fingerprint readers, iris scanners, facial scanners, or other devices that receive one or more identifying inputs from the customers.

This exemplary embodiment of a customer terminal 103 also permits a remote pharmacist or a technician to provide information to the customer. Information may be provided using dedicated output devices, represented schematically and identified by the reference numeral 188. Exemplary dedicated output devices 188 may include a drug information printer, a receipt printer, a speaker, and encoding devices for magnetic or optical data. Information may also be provided to the customer through multipurpose devices such as the video screen 174 and CCTV. It should be understood that any output device that is capable of transmitting information to the customer, whether in printed, electronic, magnetic, audible, visible, or other form, and whether encoded or directly accessible by the customer, may be used.

This exemplary embodiment of a customer terminal 103 also includes access to a pneumatic delivery system. Pneumatic delivery access opening 192, shown on the front of the customer terminal 103, provides access to a carrier which moves in a pneumatic delivery system which may be connected to one or both of the drug retrieval vault 126 and the customer service area 102. Although in this exemplary embodiment the connection between a customer terminal 103 and the customer service area 102 or the drug retrieval vault 126 is direct, as can be seen in the schematic representation of the pneumatic delivery tubes 129 and 139 in FIG. 3, in other embodiments the pneumatic delivery system may be configured as a web of interconnected pneumatic delivery tubes, with the customer, the remote pharmacist, or the technician controlling the transmission of items in appropriate carriers to one or more of a number of destinations within the system.

In this exemplary embodiment, the customer terminal 103 includes an alert button 196 to inform the remote pharmacist or the technician in the customer service area 102 that the customer is at a customer terminal 103. It should be understood that an alert button 196 is one of many means by which the remote pharmacist or the customer service technician may be alerted to the presence of a customer. Other embodiments may include more or different alert methods. For example, suitable alert mechanisms include, but are not limited to, proximity sensors, motion sensors, keyboards, weight sensing mats and drive over sensors.

As noted above, there are many possible configurations for customer terminals generally similar to customer terminal 103. Some likely configurations are suggested in FIG. 2. Two full service customer terminals are illustrated: an internal self-service terminal 104 and an external self-service terminal 110. It is also sometimes desirable to split the pharmaceutical delivery process by permitting orders to be placed at one terminal and picked up at another. Exemplary embodiments of partial service terminals illustrated in FIG. 2 include an external order terminal 106, and an external pick-up terminal 108. Although the embodiment illustrated in FIG. 2 suggests splitting the functions for the drive-up terminals on the exterior of the store, it may be desirable to separate the functions at the inside terminals as well. For example, a customer may wish to drop off an order for a prescription or other item at a customer terminal located near the front of a store, and pick it up at the customer service area 102 after shopping. The particular features of each customer terminal may be selected to accommodate customer demand, store policy, or legal requirements. However in general, each pharmacy 100 will likely include a full service terminal or a combination of partial service terminals which provide CCTV communication with the remote pharmacist, and means to accept a prescription or order, means to dispense a filled prescription or order, means to pay for the item ordered, and means to dispense any printed information that is required to be provided with the item ordered.

Figure 5:
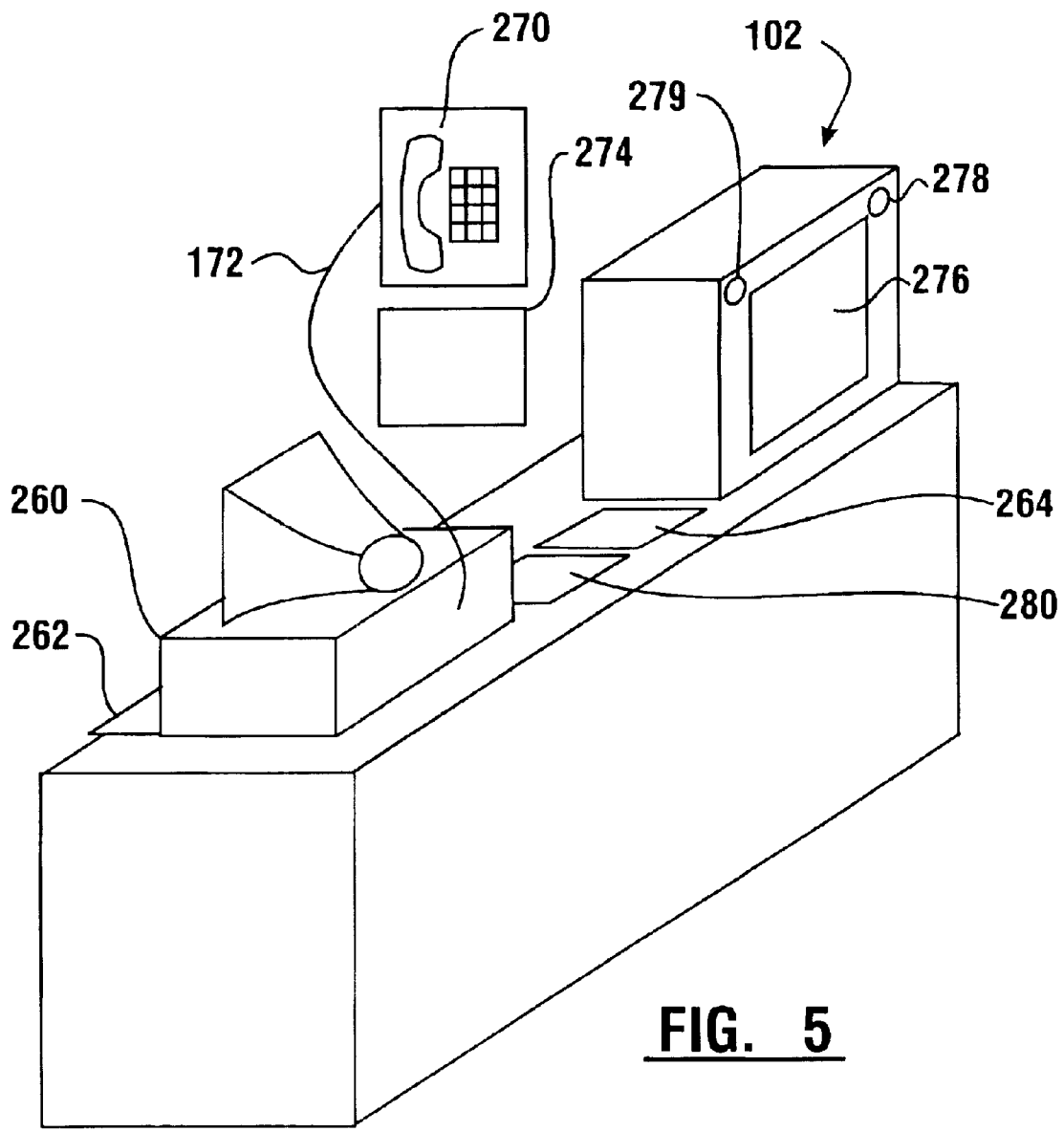
FIG. 5 is a side view of a representative customer service area.

This exemplary embodiment of a pharmacy 100 includes a customer service area 102. The customer service area 102 is represented in FIG. 5 and is generally indicated by reference numeral 102. The customer service area 102 includes a customer service terminal 260. The technician enters information into the customer service terminal 260 by using at least one input device 262, generically represented as a keyboard 261. Although in this illustration the input device 262 is depicted as a keyboard 261, in other embodiments it may include other devices which permit interactive entry of requests for pharmaceutical care into the customer service terminal 260. Such devices may include, but are not limited to, an electronic input device such as a mouse, touch screen, writing pad, or a light pen.

The exemplary customer service area 102 incorporates a customer service telephone 270. The customer service telephone 270 is connected to the customer service terminal 260, illustrated schematically and denoted by reference numeral 172. In this embodiment the customer service area 102 also incorporates a CCTV system so that the customer or the technician may speak directly with the remote pharmacist. The CCTV system is represented by the video screen 276, and includes a CCTV camera 278 and speaker 279. In addition, in this exemplary embodiment the customer service area 102 includes one or more dedicated input devices, depicted schematically and denoted by the reference numeral 264. Dedicated input devices 264 may include, but are not limited to, graffiti pads, card readers, prescription scanners, optical readers, and magnetic readers.

The customer service area 102 may also include dedicated output devices, depicted schematically and denoted by the reference numeral 280. Exemplary dedicated output devices 280 include a drug information printer, a receipt printer, a speaker, and encoding devices for magnetic, optical, or other data. Information may also be provided to the customer through multipurpose devices such as a video screen 174 or a CCTV system. It should be understood that any output device that is capable of transmitting information to the customer, whether in printed, electronic, magnetic, audible, visible, or other form, and whether encoded or directly accessible by the customer, may be used.

Finally, in this exemplary embodiment the customer service area 102 is connected to the drug retrieval vault 126 and to each of the customer terminals 103 by a pneumatic delivery system, the access opening to which is schematically depicted and referenced by the numeral 274. In this exemplary embodiment, the connections between the customer service area 102 and the customer terminals 103 or the drug retrieval vault 126 are direct, as can be seen in the schematic representation of the pneumatic delivery system in FIG. 3. It should be understood that in other embodiments the pneumatic delivery system may be configured as a web of interconnected pneumatic delivery tubes, with the customer, the remote pharmacist, or the technician controlling the transmission of items to one or more of a number of destinations in the system.

Figure 6:
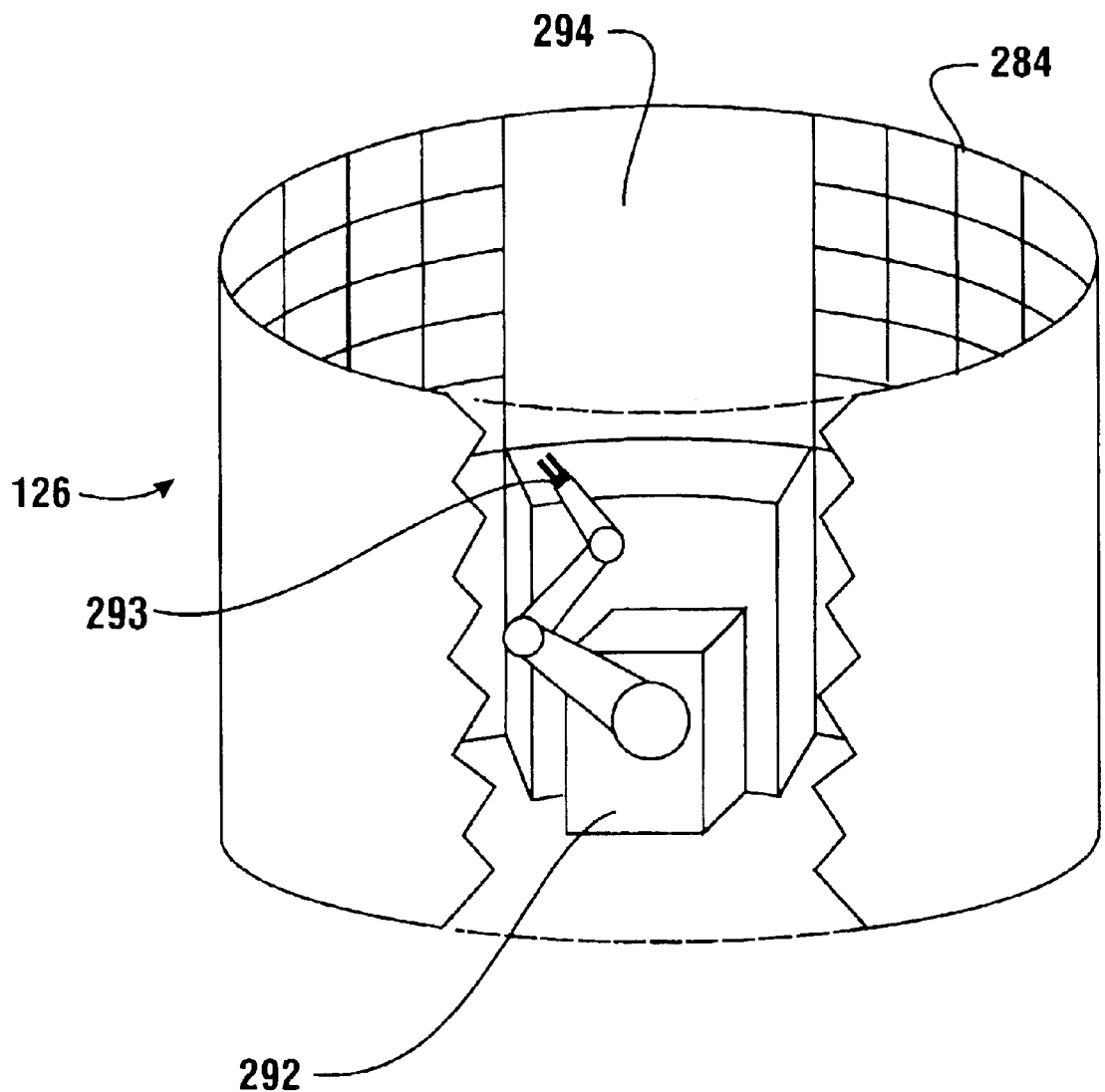
FIG. 6 is an elevated view of a drug retrieval vault.
Figure 7:
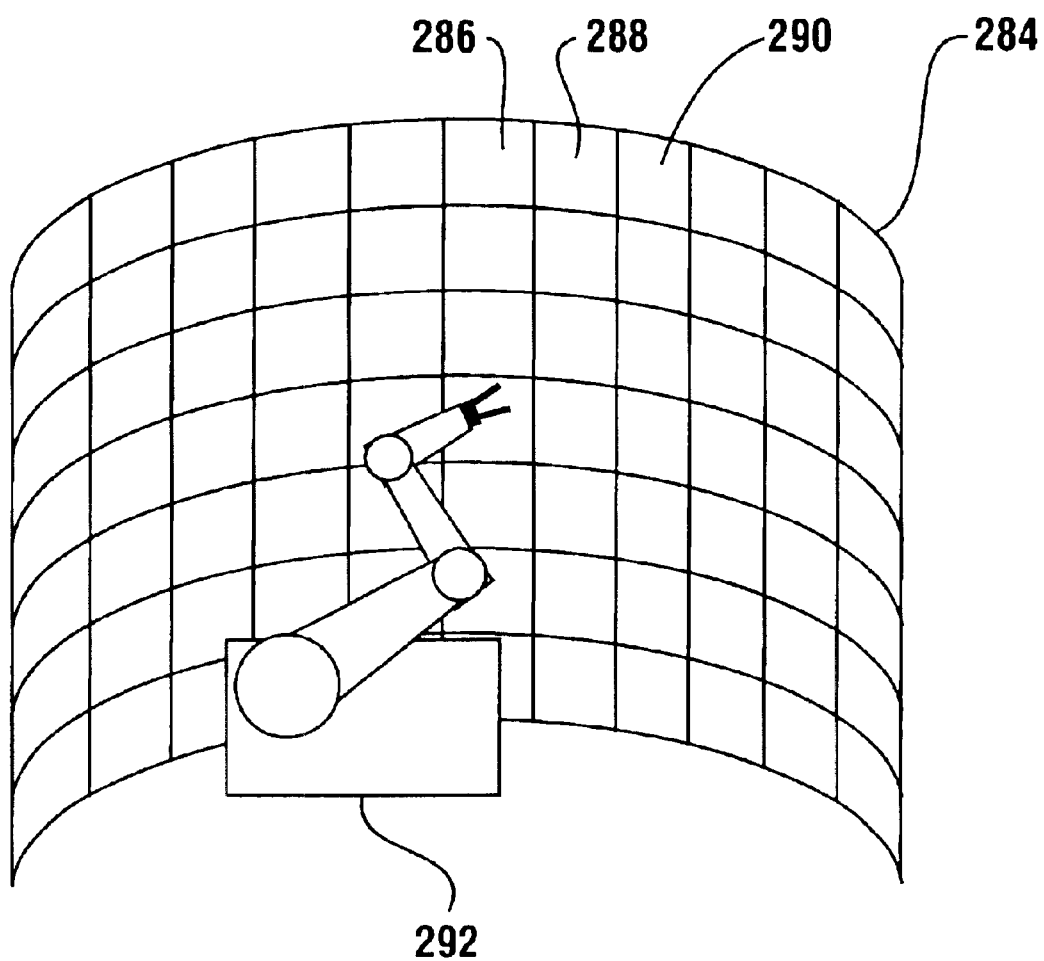
FIG. 7 is a partial cutaway view of a drug retrieval vault.

In this exemplary embodiment, preparation of pharmaceutical items may take place in two vaults, a drug retrieval vault 126 and a drug compounding vault 128. The drug retrieval vault 126 is illustrated in FIG. 6. The drug retrieval vault 126 is preferably in a secured area, accessible only to individuals who are authorized to enter it. The walls of the exemplary drug retrieval vault 126 are generally curved and incorporate a plurality of drug storage cells. In this embodiment the drug storage cells generally cover a large portion of the walls of the drug retrieval vault 126. That portion of the walls is referred to as the drug storage area 284, and is illustrated in FIG. 7. Representative individual drug storage cells are labeled 286, 288, and 290 in FIG. 7.

Prescription medications, or other items that may be ordered or needed for compounding are stored in the drug storage cells. The contents of each drug storage cell are linked in computer memory or through machine readable indicia, or both, to a unique drug storage cell location identifier, such as, for example, the x-y coordinate position of the drug storage cell, the grid position, the height and angle of rotation, or any other similarly unique identifier. The linked information is stored in a database, which is accessible to one or more of the remote pharmacist, the drug retrieval robot 292, or the technician.

Figure 8:
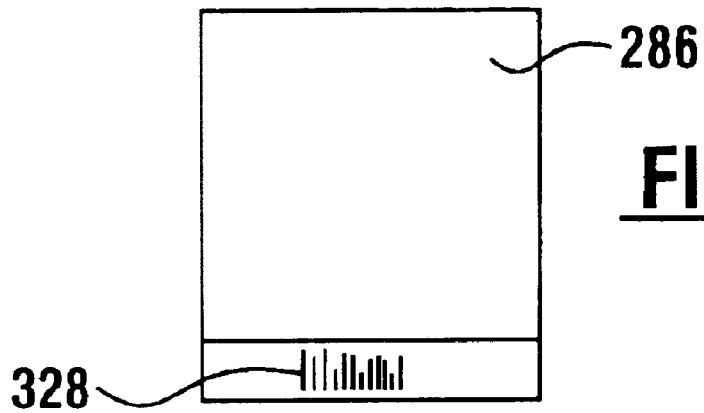
FIG. 8 is a front view of a drug storage cell.
Figure 9:
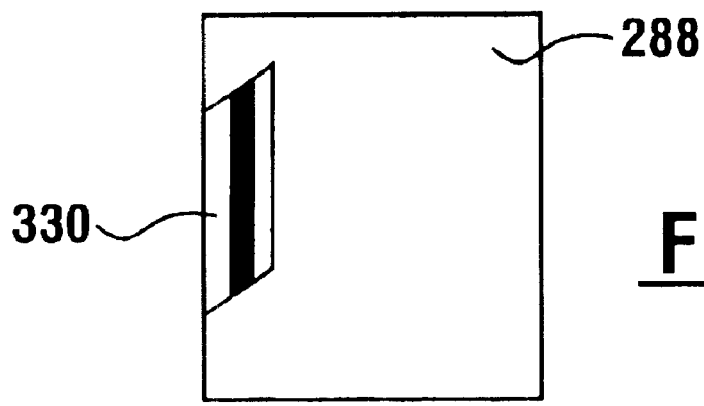
FIG. 9 is the front view of another drug storage cell.
Figure 10:
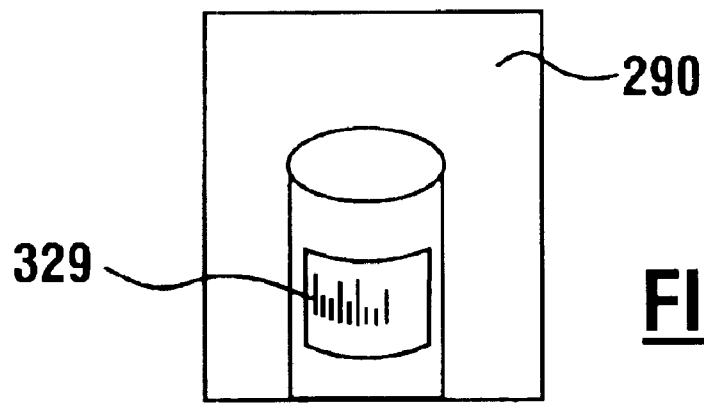
FIG. 10 is the front view of another drug storage cell which contains a bulk product.

In this exemplary embodiment additional coded information is available that may be used to verify that the contents of a particular drug storage cell match the expected contents of a particular drug storage cell. As illustrated in FIG. 8 the drug storage cell 286 contains machine readable indicia in the form of a bar code strip 328 on the front of the lower shelf of the cell 286. In FIG. 9, drug storage cell 288 contains a card with a magnetic stripe, which extends from the left side of the drug storage cell 288. In FIG. 10, the packaging of the contents of the drug storage cell 290 contains other machine readable information. In addition to information that can be used to verify the identity of the item to be dispensed, a variety of additional data may be encoded in this manner, such as packaging, inventory, drug interaction, pricing, or other information.

Figure 11:
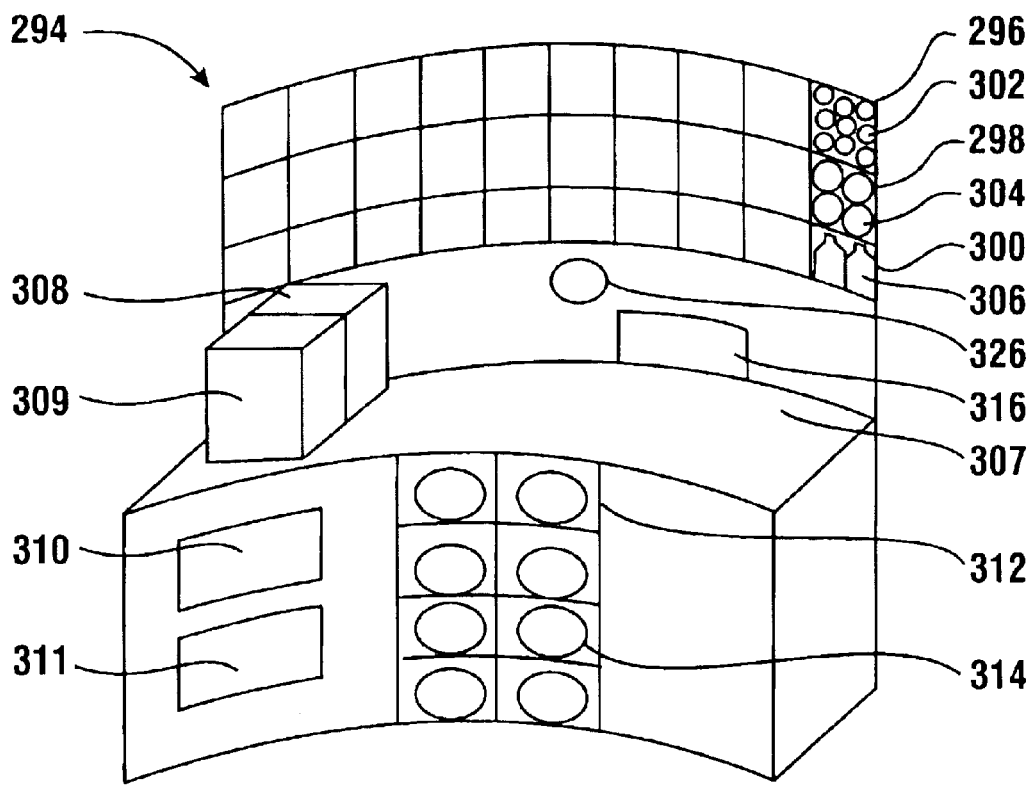
FIG. 11 is a cross-sectional view of the drug preparation area of a drug retrieval vault.

Illustrated in FIG. 11 is a different section of the wall of the exemplary drug retrieval vault 126. This section is generally referred to as the packaging wall 294. One portion of the packaging wall 294, illustrated in this embodiment as the upper portion, contains cells which hold the containers needed to package the prescriptions or items ordered by the customers. Three exemplary package cells are identified by the numerals 296, 298, and 300. Various sizes and shapes of customer packaging are shown in representative fashion and are identified by the numerals 302, 304 and 306. In addition, the exemplary packaging wall 294 contains various devices needed to quantify the pharmaceutical products requested. Shown in a representative manner on a packaging counter 307 which is attached to the packaging wall 294 are a counting device 308 and a measuring device 309. Although in this exemplary embodiment of the packaging wall 294 there are two quantifying devices, in other embodiments there may be fewer, more, or different quantifying devices. For example, a pharmacy 100 selling both pills and insulin syringes would probably not be able to use the same counting device for both. Likewise, the measuring device needed to measure an ointment would likely be different than one needed to measure a liquid. In the exemplary pharmacy 100, the drug retrieval vault 126 should contain all the measuring devices that would be needed to accurately quantify anything that is expected to be sold at the pharmacy 100.

A label printing device 310 and a drug information printer 311 are built into the exemplary packaging counter 307. In this exemplary embodiment, the packaging counter 307 also contains a storage area 312 and containers adapted to be moved within the pneumatic delivery system. Access opening 316 to the pneumatic delivery system is also located on the packaging wall 307. In this exemplary embodiment there are six pneumatic delivery tubes 130, 129, 131, 132, 133, and 134, each of which directly connects the drug retrieval vault 126 to one of the drug compounding vault 128, a customer terminal 103, and internal self-service terminal 104, a one stop external self-service terminal 106, the external pickup terminal 110, and the customer service area 102. In other embodiments the pneumatic delivery system may be configured as an interconnected web of pneumatic tubes, with the customer, the remote pharmacist, or the technician controlling the transmission of items to one or more of a number of destinations in the system. In still other embodiments, the pneumatic delivery system may be a combination of individual straight line delivery systems and an interconnected system of tubes with multiple destinations.

As shown in FIG. 6, in the center of the exemplary drug retrieval vault 126 is a drug retrieval robot 292. The drug retrieval robot 292 in this exemplary embodiment is adapted through the operation of one or more computers to perform at least some of the following: (1) receive directions from a remote pharmacist; (2) deliver information to a remote pharmacist; (3) locate a particular drug storage cell; (4) read the information encoded and attached to the cell or to the contents of the cell; (5) verify that the contents of the cell are those that were expected; (6) retrieve an item from the storage cell; (7) move selected items to the preparation area; (8) deliver selected items to the drug compounding vault 128; (9) count a specified quantity of the selected item; (10) measure a specified quantity of the selected item; (11) retrieve an appropriate container for the selected and quantified item; (12) put the selected and quantified item in the selected container; (13) retrieve prepared items from the drug compounding vault 128; (14) retrieve a label from the printer; (15) retrieve a drug information sheet from the printer; (16) place the label onto the container; (17) display the selected item and the dispensed item to the remote pharmacist via CCTV; (18) deliver the packaged item to the appropriate customer terminal or customer service area 102 via a pneumatic delivery system; (19) deliver drug information sheets to a customer terminal 103 via a pneumatic delivery system; or (20) other tasks necessary to prepare a pharmaceutical order.

The drug retrieval robot 292 is adapted to perform these tasks at the direction of a remote pharmacist. While the remote pharmacist generally directs the actions of the drug retrieval robot 292, some of the subroutines necessary to perform these tasks may be preprogrammed into computers in operative connection with the drug retrieval robot 292 so that the remote pharmacist is not required to direct the actions of the drug retrieval robot 292 in minute detail.

The exemplary drug retrieval robot 292 is equipped with a camera 293 which is connected with the CCTV system, and which may be aimed by the remote pharmacist at areas within the drug retrieval vault 126. In addition, there may be one or more cameras contained in the walls of the drug retrieval vault 126 connected with the CCTV system, which are controllable by the remote pharmacist and which permit the remote pharmacist to view activity within the drug retrieval vault 126. One such CCTV camera is located along the packaging wall, and is indicated by the reference numeral 326 in FIG. 11.

Figure 12:
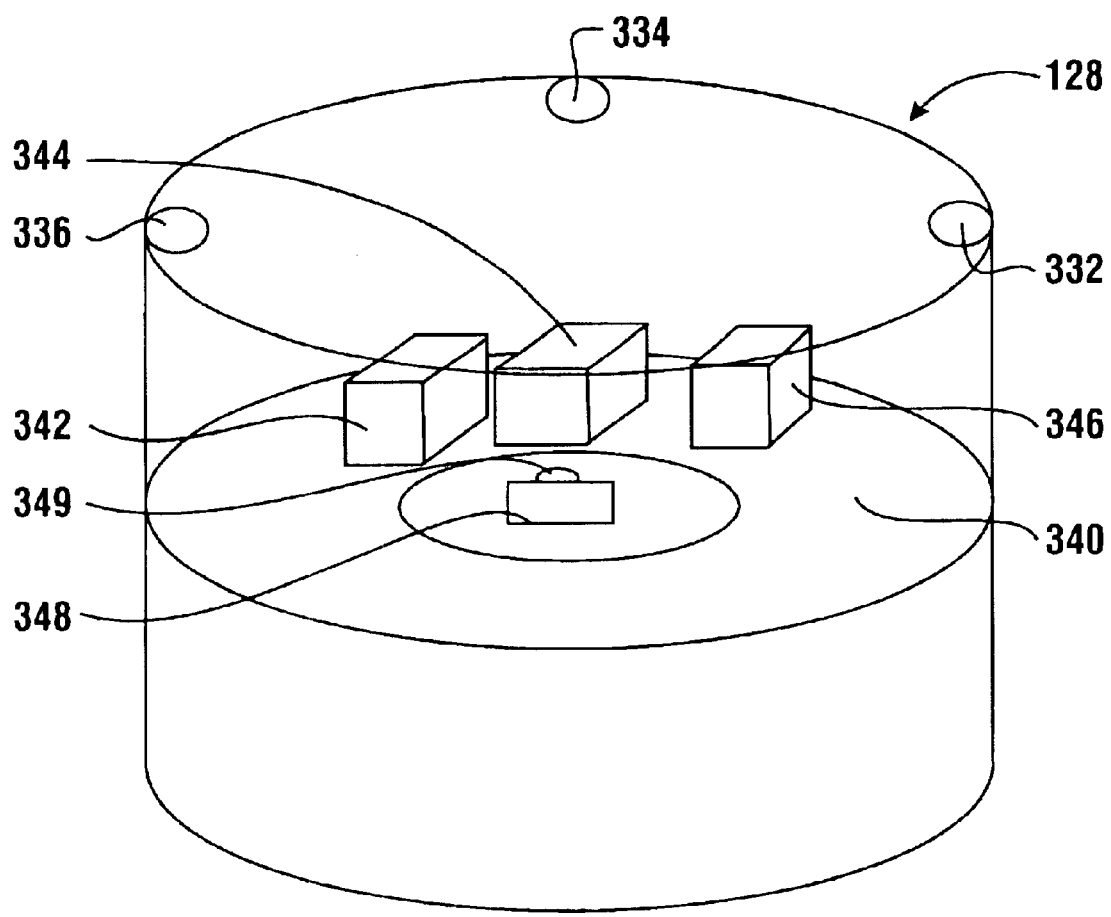
FIG. 12 is an elevated view of a drug compounding vault.

FIG. 12 illustrates an exemplary drug compounding vault 128. The drug compounding vault 128 is preferably a secured area, accessible only to individuals who are authorized to enter it. In this exemplary embodiment, a compounding shelf 340 extends horizontally inward from a portion of the wall of the drug compounding vault 128. Various compounding devices, schematically shown and indicated by reference numerals 342, 344, and 346 are located on the compounding shelf 340. In addition to the compounding devices, the compounding shelf 340 may also contain various quantifying devices, similar to those contained in a drug retrieval vault 126. The drug compounding vault 128 may also contain various packages for packaging the compounded items, similar to those contained in the drug retrieval vault 126.

A compounding robot 348, schematically represented, is situated in the drug compounding vault 128. An exemplary compounding robot 348 in a drug compounding vault 128 of this invention will be able to do one or more of the following: (1) receive communications from a remote pharmacist, including detailed directions for compounding a particular medication; (2) retrieve the individual components of a prescription from the pneumatic delivery system; (3) count a specified quantity of the selected item; (4) measure a specified quantity of the selected item; (5) retrieve an appropriate container for the selected and quantified item; (6) put the selected and quantified item in the selected container; (7) use the various compounding devices located in the compounding vault to prepare medications that require compounding; (8) display the individual ingredients to the remote pharmacist via CCTV; (9) display the compounding process to the remote pharmacist via CCTV; (10) display the completed product to the remote pharmacist via CCTV; (11) deliver the completed product to the drug preparation vault via the pneumatic delivery system or (12) other tasks necessary to compound medications.

Four CCTV cameras, three of which are shown and indicated by the reference numerals 332, 334, 336, are located near the top of the wall of the exemplary drug compounding vault 128, at positions roughly equidistant from each other. In this exemplary embodiment, the cameras 332, 334, 336 may be manipulated by the remote pharmacist in order to monitor aspects of the compounding process. A compounding robot 348 in an exemplary embodiment also contains a CCTV camera 349 that may be manipulated by the remote pharmacist to monitor the details of compounding process. It should be understood that although this exemplary embodiment includes four CCTV cameras, other embodiments may include more or fewer cameras, and the cameras may be placed in different locations than those depicted in FIG. 12.

Figure 13:
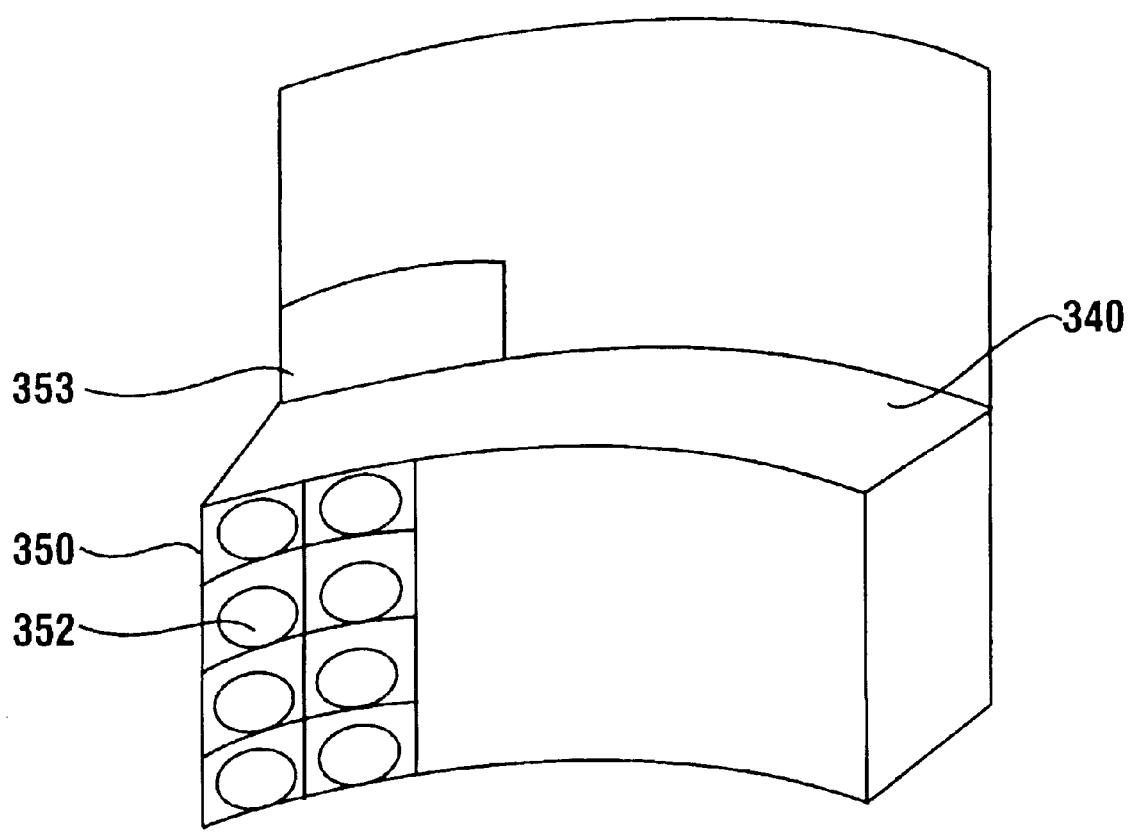
FIG. 13 is a partial cutaway view of a transmission area of a drug compounding vault.

FIG. 13 shows a cutaway portion of the drug compounding vault 128. The portion illustrated in FIG. 13 is the communication center of the drug compounding vault 128. The container storage area 350 and containers 352 adapted for placement in pneumatic carriers are located below the compounding shelf 340 in the drug compounding vault 128. Carriers may be of various types, such as for example carriers of the types shown in U.S. Pat. Nos. 5,131,792; 5,304,017; or 4,715,750, the disclosures of which are incorporated herein by reference. In this exemplary embodiment, the access opening 353 to the pneumatic delivery tube 130 is located above the compounding shelf 340. In this exemplary embodiment, the pneumatic delivery tube 130 directly connects the drug retrieval vault 126 to the drug compounding vault 128. In other embodiments, a pneumatic delivery system may be configured as an interconnected web of pneumatic tubes, with the customer, the remote pharmacist, or the technician controlling the transmission of items to one or more of a number of destinations in the system.

Although in this exemplary embodiment there are two separate vaults in which the preparation of prescriptions or other items takes place, in other embodiments there may be only one vault in which preparation occurs. A single vault may contain one, two, or more robots, or other item handling devices, and may include each of the items that are contained in one or the other of exemplary drug retrieval or compounding vaults 126 or 128. In still other embodiments, there may be more than two vaults for a particular pharmacy 100, or the components of each of two vaults may be different than the exemplary vaults described above, as may be appropriate to meet the needs of each individual pharmacy or pharmaceutical system.

The connection between the two geographically remote portions of the exemplary pharmaceutical system is now discussed. Returning to FIG. 1, in the method of operation of an exemplary embodiment, a single remote pharmacist is operatively linked to a number of individual pharmacies 96, 98, 100. In this exemplary embodiment, the remote pharmacist is remote from all of the individual pharmacies 96, 98, 100 in which he controls the operations. In other embodiments, despite the term used here, the remote pharmacist may be located in one pharmacy, for example, pharmacy 96, and operatively linked to the remaining pharmacies 98, 100 over which the remote pharmacist has authority. Although in this embodiment, the remote pharmacist is shown as operatively linked to three pharmacies 96, 98, 100, in other embodiments the remote pharmacist may be linked to fewer or more pharmacies.

There are two primary links in the exemplary system between the remote pharmacist and the individual pharmacies 96–100. One link is through the CCTV system. In an exemplary embodiment, a remote pharmacist has at least one CCTV camera 164 including audio and video communication devices, through which the remote pharmacist may communicate with customers at customer terminals 103 in each pharmacy 96–100. In this exemplary embodiment, the CCTV display uses a separate video screen 163. In other embodiments, there may be more than one video screen, or the CCTV display may appear on the pharmacist terminal 260.

A second link includes the pharmacist computer 140, which is operative to communicate with the pharmacy computer 114 through network 138. The transmission of prescription or order information, and the directions to the drug retrieval and compounding robots 292 and 348, for example, may use this link. In order to protect the integrity of the exemplary system, both the pharmacist computer 140 and the pharmacy computer 114 may utilize firewalls, encryption techniques, and/or other security measures to prevent unauthorized access. Interactions involving any customer terminal 103, the customer service terminal 260, or the drug retrieval and compounding robots 292 and 348, and an individual or computer outside the pharmacy 100, must be authorized by the pharmacy computer 114. Similarly, external interactions with any portions of the system that are controlled by the pharmacist computer 140 must be authorized by the pharmacist computer 140. The pharmacist computer 140 may also utilize a firewall, encryption techniques, and/or other security measures to prevent unauthorized access.

The remote pharmacist in the exemplary embodiment has access through the pharmacist computer 140 to various databases including, for example, a patient history database 144, a drug database 148, and a rules database 152, as shown in FIG. 1. These databases are connected to the pharmacist terminal 162 directly or through one or more wide area or local area networks 142. In addition, the pharmacist terminal 162 is also adapted to access external databases 156 through the pharmacist computer 140 and one or more networks 138. An exemplary external database is represented schematically in FIG. 1, and identified by the reference numeral 156.

In addition to being adapted to access databases, the pharmacist terminal is adapted to permit a remote pharmacist to do one or more of the following tasks: (1) interact with a pharmacy technician, (2) interact with a customer, (3) accept prescription or order and insurance information, (4) initiate the transmission of prescription or order and insurance information in the absence of a technician, (5) manipulate the drug retrieval robot 292, (6) manipulate the drug compounding robot 348, (7) manipulate the cameras in the drug retrieval and compounding vaults 126, 128, (8) control operation of printers and other dedicated output devices in the drug retrieval vault 126, customer terminal 103, and the customer service area 102 to output information that may be provided to the customer, (8) prepare a list of concerns related to a particular customer's use of the item ordered, (9) direct the display of information on multipurpose devices at a customer terminal 103 or the customer service area 102, (10) determine the price to be charged for a particular order, including adjusting for insurance payments, (11) direct the delivery of packaged products through the pneumatic delivery system, and (12) other tasks necessary to the remote operation of an automated local pharmacy.

The Operation of the Exemplary Pharmaceutical System

Figure 14:
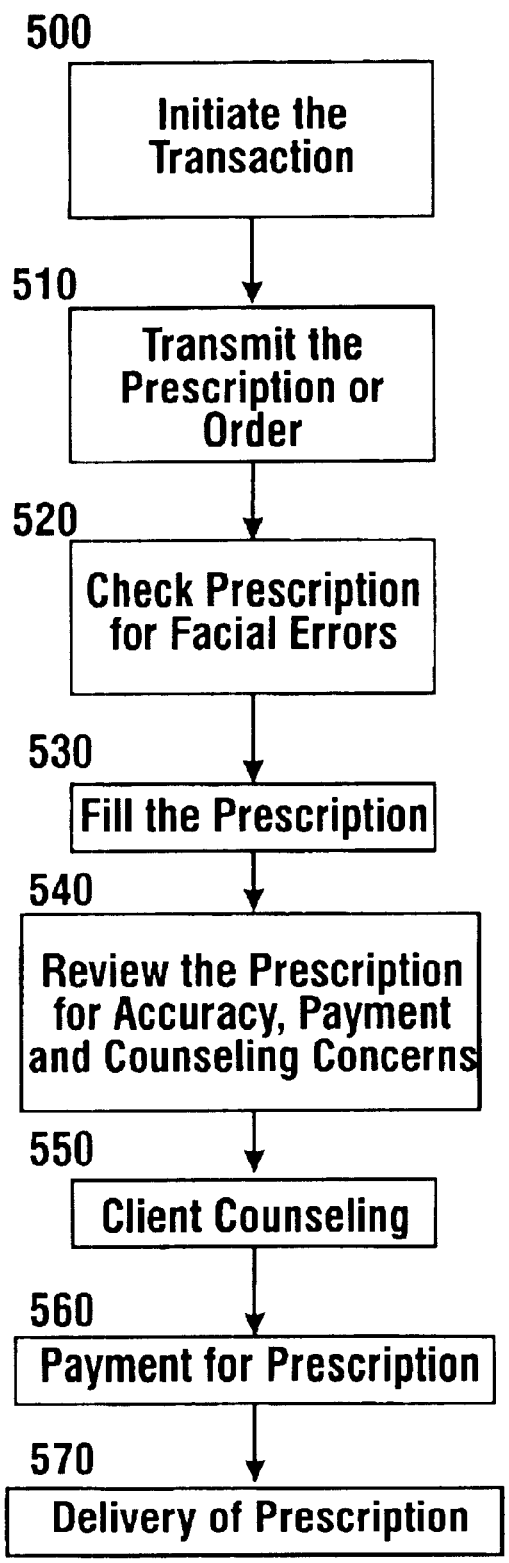
FIGS. 14 through 16 are flow charts representing a method operating a pharmaceutical system of this invention.

FIG. 14 schematically represents an overview of an exemplary transaction flow used in processing a prescription in the exemplary pharmacy system previously described. Initially, the prescription is presented to a local pharmacy 100 and transmitted to a remote pharmacist, as indicated in steps 500 and 510. Once the prescription is received by a remote pharmacist, it is initially reviewed for facial accuracy, and steps are taken to resolve any facial errors, as indicated in step 520. As noted in step 530, the remote pharmacist then fills the prescription. This is done by directing the drug retrieval robot and compounding robots 292 and 348 in the local pharmacy 100 where the order originated to prepare the prescription. In this exemplary embodiment, as represented in a step 540, once the prescription is prepared, additional checks are performed to ensure that the prescription was accurately filled, to guide patient counseling, and to accurately price the prescription. Following this second review of the prescription, the remote pharmacist may offer to counsel the customer, payment is made, and the medication or other item is delivered, as represented in steps 550–570.

With minor variations, the same steps may be followed for the purchase of a nonprescription item which is required to be distributed through the pharmacy. Examples of such items include cough medication containing small amounts of narcotics, insulin syringes, or other items that do not necessarily require a prescription but may be subject to abuse. It should be understood that any reference to a prescription includes other items, the distribution of which must be made through the pharmacy.

Transmission of a Prescription

Figure 15:
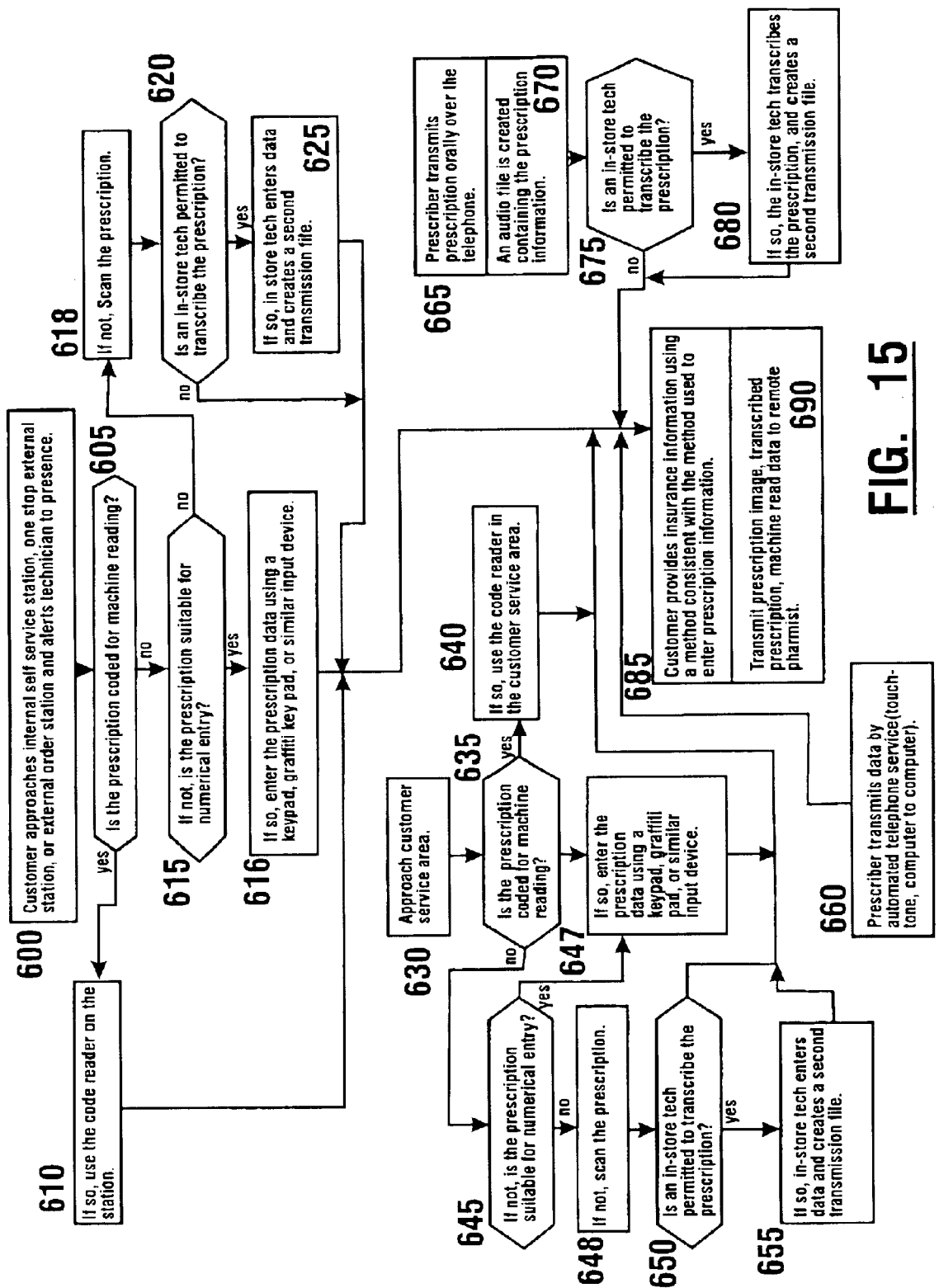

The initiation of the transaction and the transmission of the prescription to the remote pharmacist, steps 500 and 510 in FIG. 14, are illustrated in more detail in FIG. 15. In an exemplary embodiment there are four ways to initiate a request for a pharmaceutical or other item. These are represented beginning with steps 600, 630, 660, and 665 respectively. Steps 600 through 625 represent what occurs if a customer uses a customer terminal 103 to present a prescription, or other order, to the remote pharmacist.

Steps 630 through 655 describe the process followed if the customer presents the prescription directly to a technician staffing the customer service area 102. Step 660 represents the direct transmission of a prescription or order to the pharmacy 100 by an automated means. Finally, steps 665 through 680 describe the transmission of a prescription to a technician over the telephone by a prescriber 170.

Returning now to the first method for transmitting the prescription, as described in steps 600 through 625. In this embodiment the customer places the order by means of a customer terminal 103. The customer terminal 103 may be internal or external, and may be a full service terminal or a terminal adapted to accept orders for pickup at another location.

As represented in a step 600 in FIG. 15, the customer approaches the customer terminal 103 and alerts the technician in the customer service area 102 by pressing the alert button. Although in this exemplary embodiment the technician is alerted by means of an alert button 196, it should be understood that any number of suitable alert mechanisms may be used, some of which are described above.

After alerting the technician that a customer is waiting, the customer will present the prescription to the technician. How the presentation is presented will depend on the form of the prescription. The prescription will likely be in one of three forms. It may be in an encoded form suitable for machine reading, in numerical form suitable for keypad entry, or handwritten. Suitable formats for machine reading would include bar coding, optical characters, or magnetic coding. As represented in steps 605 and 610, if the prescription is coded for machine reading the customer is directed to use the appropriate reader on the customer terminal 103 for reading machine readable indicia. Once read, the prescription data is electronically transmitted to the technician.

If the prescription is not in a format suitable for machine reading, it may be in a format suitable for keypad entry, as represented in a step 615. A prescription refill is one example of a request for pharmaceutical care that is generally in numerical format and is suitable for keypad entry. Such prescriptions may be entered using a keypad or graffiti pad, represented in step 615. Once entered, the prescription data is electronically transmitted to the technician.

Finally, the prescription may not be coded for machine reading, and may not be suitable for keypad entry. Most handwritten prescriptions fit this category. If the prescription is of this nature, indicated by a negative response to both of the queries in steps 605 and 615, the customer scans the prescription or other order using the prescription scanner 178, as indicated in a step 618. The image of the prescription is electronically transmitted to the technician. In some instances a technician may be permitted to transcribe the prescription, in others a pharmacist may be required to do the transcription as determined in a step 620. If a technician is permitted to transcribe the prescription, as is represented in a step 625, the technician will enter the data from the image into an electronic form presented on the pharmacy computer 114. If the technician is permitted to transcribe the prescription, the technician will send both the transcribed file, and the file containing the scanned prescription image to the remote pharmacist, otherwise the technician will transmit only the image file to the remote pharmacist.

Another exemplary method of initiating the transaction is for the customer to go to the customer service area 102 in the store, as represented in a step 630. As previously described, the customer service area 102 is adapted to accept a prescription or order in any of the formats acceptable for the mechanical prescription transmission discussed above. If the prescription is coded for machine reading, determined in a step 635, the customer or the technician uses the appropriate reader at the customer service area 102 to create a file containing the order, as represented at step 640. If the prescription consists of information that may be entered using a keypad, determined in a step 645, the customer or technician enters the prescription data using a keypad or graffiti pad, described in a step 640. On the other hand, if the prescription is not suitable for either machine reading or keypad entry, the prescription is scanned to create an image file, as represented in a step 645. If a technician is permitted to transcribe the prescription, as determined in a step 650, then a technician also enters the data into a facsimile form in the customer service terminal 260, and creates both an image file and a data file.

In addition to a customer bringing a prescription to a pharmacy 100 it is also customary for pharmacies to accept prescriptions directly from a prescriber 170. In an exemplary embodiment, a prescriber 170 may transmit the data directly to the customer service terminal 260 by a semi-automated means, such as using the touch tone buttons on the telephone, as represented in a step 660. A prescriber 170 may also, or alternatively, transmit a data file over telecommunication lines from the prescriber's computer 171 to the customer service terminal 260.

In addition, a prescriber 170 may use a more traditional means of transmitting the prescription, such as verbally relaying the information to the technician over the telephone, as represented in steps 665–680. The technician will create an audio file, which may be either analog or a digital, in a format that can be sent to the remote pharmacist, as represented in a step 670. In some instances, a technician may be permitted to transcribe the prescription or order information. If so, as determined in a step 675, the technician transcribes the information into a format that can be transmitted to the remote pharmacist, and prepares a second file for transmission to the remote pharmacist, as represented in a step 680. This may be accomplished, for example, by entering the data into a facsimile form presented on a customer service terminal 260.

In addition to transmitting prescription data, a customer may also transmit insurance information by any of the means described above that is adapted to accept the format in which the insurance information is presented, as represented in a step 685. Once the prescription or order information and any insurance information has reached the customer service terminal 260, the technician may transmit the prescription and insurance information to the remote pharmacist through the pharmacy computer 114 over a network 138, as represented in a step 690. In some cases, as indicated in steps 655, 625, and 675, the technician may reformat the information and create a prescription facsimile data file to be transmitted to the remote pharmacist along with the audio or visual image file of the prescription and the insurance information. In some embodiments the insurance information may be routed to another computer or service provider that can validate and/or process payments based on the insurance information.

Although in the exemplary embodiment, the prescription or order information is presented first to a technician at the customer service area 102, in some embodiments there may not be a technician present in the pharmacy 100, or the technician may be occupied with other tasks. If the order is being placed by a customer at a customer terminal 103 without the intervention of a technician, the remote pharmacist will be alerted to the initial presence of the customer. When the customer transmits information from the customer terminal 103 to the customer service terminal 260, the remote pharmacist will access the customer service terminal 260 over the network 138 through the pharmacy computer 114 and cause the transmission of the order and insurance information from the customer service terminal 260 to the pharmacist terminal 162.

If the order is being placed by a prescriber 170 over the telephone or by an electronic transmission without the intervention of a technician, the customer service terminal 260 may verify with the pharmacy computer 114 that the prescriber 170 is an authorized prescriber. This may be done using various techniques such as passwords, digital signatures, or other suitable verification techniques. Once the prescriber 170 is verified as an authorized prescriber, the customer service terminal 260 may accept the prescription or order and prepare it for transmission to the remote pharmacist. Similarly, if no technician is available and a customer telephones a request for a refill of a prescription, the pharmacy computer 114 may verify that the prescription is valid, that there are remaining refills, and that the prescription has not expired. If so, it may accept the prescription or order and prepare it for transmission to the remote pharmacist.

When the customer service terminal 260 has received data corresponding to a valid prescription, it may notify the remote pharmacist, by using the pharmacy computer 114 to transmit a message to the pharmacist computer 140 over the network 138. The remote pharmacist may then authorize the customer service terminal 260 to transmit the prescription file or files to the pharmacist terminal 162.

The mechanism by which an order reaches a remote pharmacist without the intervention of a technician may vary from the description above. A desirable feature, however, includes verification by a gatekeeper, such as the pharmacy computer 114 or a pharmacist computer 140, that the prescription is authorized by an individual who is permitted to write prescriptions or, if a refill, that the prescription on file is still valid.

Remote Pharmacist

Turning in more detail to an exemplary procedure followed by the remote pharmacist, initially the remote pharmacist verifies whether there are facial errors in the prescription which might prevent it from being filled, represented in a step 520 in FIG. 14. Facial errors are those apparent from the face of the prescription. Examples of this kind of error include a prescription that is missing information that is required by law, a prescription which orders an amount of medication that does not match the instructions for using it, or one that is missing a prescriber's name, or one that appears to have been tampered with, for example. If there are facial errors in the prescription, the remote pharmacist follows the pharmacy or state mandated policy and/or organizational policy to correct those errors or to reject the prescription or order. Although in this exemplary embodiment, any facial errors in the prescription are discovered and corrected as a preliminary step, in other embodiments some of the verification of facial accuracy may be delayed until the second review of the prescription, represented in a step 540 in FIG. 14, as long as the prescription or order contains enough information to determine which item is being ordered and what quantity is to be dispensed. In still other embodiments, this initial review may be more extensive, and may include some of the reviews described as being performed during the second review.

Once the prescription is in condition to be filled, the remote pharmacist provides inputs operative to cause the connected computers to direct robots 292 and 348 in the two drug vaults 126 and 128 to prepare the prescription for the customer. An exemplary form of this process is represented schematically in FIG. 16. The remote pharmacist must initially decide whether filling the prescription will involve only the drug retrieval robot 292, or both the drug retrieval and the compounding robot 348. This decision is represented in a step 800. If the prescription or order requests something which is pre-packaged or which may be selected and quantified, the remote pharmacist will send instructions to the drug retrieval robot 292 to obtain the item and to prepare it for delivery to the customer. This process is represented in steps 810 through 865.

The group of items that may be prepared solely by the drug retrieval robot 292 in the exemplary embodiment are divisible into two categories. One category comprises those items that are prepackaged for delivery. Antibiotic packs and tubes of ointment, for example, are often prepackaged for sale. The other category of the items that can be prepared solely by the drug retrieval robot 292, are those that are not yet packaged for delivery. Whether the items are prepackaged or need to be quantified, the initial steps are the same, and are represented in steps 810–825 in FIG. 16.

The remote pharmacist directs the drug retrieval robot 292 to retrieve the desired item by directing it to the drug storage cell containing that item, as represented in a step 810. The location of the drug storage cell may be determined with reference to a data file which contains information linking a particular item to a particular drug storage cell. The identification of the drug storage cell may be done by the remote pharmacist, with the remote pharmacist directing the drug retrieval robot 292 to the identified location. In the alternative, the remote pharmacist may direct the drug retrieval robot 292 to retrieve a particular item, relying on locating subroutines that have been preprogrammed into a computer linked to the drug retrieval robot 292 to determine the specific location of the requested item. Once the item is retrieved, the drug retrieval robot 292 is directed to verify that the item retrieved is the item requested, as represented in a step 820. This verification may be accomplished by comparing the information encoded on the drug storage cell or on the packaging of the selected item with the data file containing the linked content and location information.

At this point, the item may be ready for labeling, as determined in a step 825. On the other hand, if the item needs to be measured or counted, additional steps, including those represented in steps 835–850, must be performed before the order is ready to be labeled. If quantification is required, once the item has been retrieved and its identification verified the remote pharmacist operates or directs the drug retrieval robot 292 to measure or count the medication. If the item ordered requires counting, as determined in a step 830, the remote pharmacist directs the drug retrieval robot 292 to use the appropriate counting device 308, and to count the number of pills or objects to be dispensed, as represented in a step 835. If the medication is a liquid or a powder, and needs to be measured instead of counted, the remote pharmacist directs the drug retrieval robot 292 to use the appropriate measuring device 309 to measure the correct quantity to be dispensed, as represented in a step 840.

Once the item has been measured or counted, the remote pharmacist directs the drug retrieval robot 292 to select an appropriate package, based on the nature and quantity of the item ordered, represented in a step 845. The remote pharmacist may select the appropriate package, and direct the drug retrieval robot 292 to retrieve it. In the alternative, the remote pharmacist may direct the drug retrieval robot 292 to use packaging information to select and retrieve the proper package. Packaging information may be stored in the bar code, magnetic code, or other indicia attached to the drug retrieval cell or to the bulk package associated with the ordered item. Although in this exemplary embodiment, the remote pharmacist 161 directs the drug retrieval robot 292 in the package selection process, in other embodiments a computer linked to the drug retrieval robot 292 may be programmed with subroutines to perform part or all of this task automatically, once a particular item and quantity have been requested by the remote pharmacist.

After the package is selected and the item ordered is quantified, the remote pharmacist directs the drug retrieval robot 292 to dispense the quantified item into the selected package and to seal the package, as represented by a step 850. Although in this exemplary embodiment, the remote pharmacist directs the packaging process, in other embodiments part or all of the process may be carried out using preprogrammed subroutines resident in a computer linked to the drug retrieval robot 292.

Figure 16:
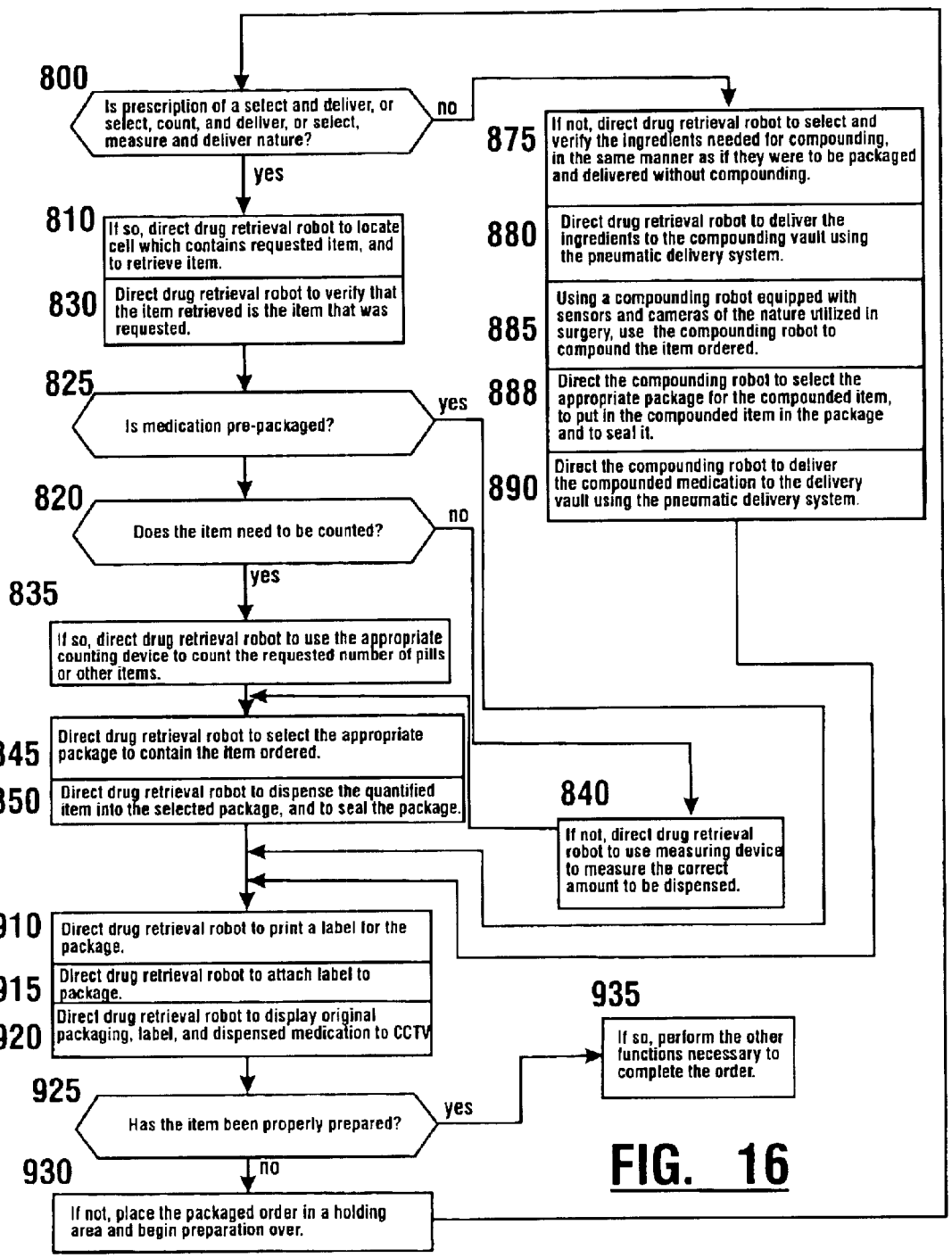

As represented in FIG. 16, steps 875–890, there are some medications that require more preparation than selecting, or selecting and quantifying. In that event the remote pharmacist directs the drug retrieval robot 292 to retrieve the appropriate components to produce the medication requested and to deliver them to the drug compounding vault 128 using a carrier transmitted through the pneumatic delivery tube 130, as represented in steps 875 and 880. The carrier is opened through actions of the compounding robot. Each component is selected and its identification verified in the manner described above. Once the components have arrived at the drug compounding vault 128 the remote pharmacist directs the motions of the compounding robot 348 to compound the requested item, as represented in a step 885. The remote pharmacists uses the network 138 and remote control devices, such as virtual reality glasses and tactile input devices, or similarly sophisticated software and devices to control the movements of the compounding robot 348.

In a manner similar to that described above, the pharmacist directs the compounding robot 348 to measure each item when it is needed, and to use the compounding tools available to mix the items together to form the medication ordered.

In this exemplary embodiment the drug retrieval robot 292 selects each bulk package that contains an ingredient that is needed and transmits it to the compounding robot 348. The compounding robot then measures the raw ingredients and compounds the medication. In other embodiments, the remote pharmacist may direct the drug retrieval robot 292 to measure the ingredients, and to send only the quantity required by the drug compounding robot 348 for compounding. Of course in other embodiments other approaches may be used.

In the exemplary embodiment, after using the compounding robot 348 to prepare the requested medication, the remote pharmacist directs the compounding robot 348 to select an appropriate package, to put the compounded medication in the selected package, as represented by a step 888, and to return the compounded medication to the drug retrieval vault 126, represented by a step 890. In this exemplary embodiment, the compounding robot 348 selects and retrieves the package for the compounded product. In other embodiments, the drug retrieval robot 292 may select the appropriate package and send it to the compounding robot using the pneumatic delivery tube 130.

Returning to the overall process, once the medication is packaged for delivery to the customer, whether it was prepackaged, required counting, required measuring or compounding, it may be labeled. The remote pharmacist directs the label printer 310 to print an appropriate label for item ordered, represented as a step 910. The drug retrieval robot 292 is then directed to attach the label to the package, as indicated in a step 915. The remote pharmacist may also direct the drug information printer 311 to print the appropriate drug information sheet for the medication prepared.

In this exemplary embodiment the tasks necessary to prepare prescriptions or other orders are split between two separate vaults, and performed in part by each of two separate robots. In other embodiments all of these tasks may be performed by a single robot in a single vault. In further embodiments, these tasks may be split differently, or may be accomplished in more than two vaults or by more than a single robot in each of one or more vaults.

The next step in the exemplary embodiment is for the remote pharmacist to verify that the medication is ready to be delivered to the customer. After the package is labeled, the remote pharmacist directs the drug retrieval robot 292 to position the original packaging and the labeled medication or other item so that the label is visible to the remote pharmacist via CCTV camera 326, or another appropriate camera, as represented in a step 920. In an exemplary embodiment the pharmacist terminal 162 may display a split screen. One side of the screen may contain the image of the prescription as it was transmitted to the remote pharmacist. If both a prescription image and a facsimile generated from encoded or transcribed data are available, both may be displayed. If the prescription was ordered verbally, the remote pharmacist may also play the audio file or a computer generated text version or other record of the audio file.

The other half of the screen may include one or more images from the drug retrieval vault 126, including the original packaging of the item being dispensed and the product that is packaged for delivery to the customer. The remote pharmacist may use these images and audio files to verify that any transcription of a prescription or order is accurate, and that the medication being dispensed to the customer is the medication that was prescribed for that customer, as represented by a step 925.

Although in this exemplary embodiment, a split screen is used to display both the request and the product that was packaged in response to that request, the verification may be performed in other ways such that it generally includes (1) comparing any transcription to the audio or visual image of the original prescription or order and (2) comparing the order to the packaged product. It should also be understood that verifying the accuracy of any transcription may alternatively be done during the earlier review, represented as a step 520 in FIG. 14, rather than during the second review, represented as a step 540 in FIG. 14.

If the remote pharmacist has any concerns about whether the packaged product matches the prescription or order, the remote pharmacist in the exemplary embodiment may retrieve additional information to verify the accuracy of the prepared product. The remote pharmacist has access to the prescription transmission data, data from the bar code or the magnetic strip of the drug storage cell, data that was encoded on the packaging of the item selected from a particular cell, the link data identifying the item that should have been in a particular drug storage cell, a video recording of the compounding process, and visual images from the selection and compounding process as captured by the CCTV cameras. In addition, the remote pharmacist has the ability to direct the drug retrieval robot 292 to manipulate the packaging or to point cameras, contained in the drug retrieval and compounding robots 292 and 348, or in the walls of the drug retrieval and compounding vaults 126, 128, at selected drug storage cells or anything else within the drug retrieval vault 126 or the drug compounding vault 128. Finally, the drug database 148 that is linked to the pharmacist terminal 162 contains images of the medications and other items that may be prescribed or ordered. The remote pharmacist can also direct the drug retrieval robot 292 to open the prepared package so that the contents can be compared to the image of the item that should have been dispensed.

If the concerns cannot be resolved, the remote pharmacist may direct the drug retrieval robot 292 to place the medication in a holding area for appropriate disposal or restocking at a later time, and to refill the prescription, as represented in a step 930 in FIG. 16.

Once the prepared product matches the written prescription or order, the remote pharmacist may perform additional reviews, and other tasks necessary to prepare the ordered item for delivery to the customer, as represented in a step 935. In this exemplary embodiment the remote pharmacist compares the prescription or order to various resident databases 148 and 152, or external databases 156 to verify that the physician is correctly identified, and that the dosage dispensed is within the suggested dosage range for that particular medication. If the remote pharmacist discovers a discrepancy, the remote pharmacist follows a preestablished policy or procedure to correct the discrepancy.

The pharmacist computer 140 also compares the prescription or order to the individual patient history in the patient database 144 to reveal any potential drug interactions or allergies that may indicate the customer should use caution or avoid using the medication or item ordered. In addition, the pharmacist computer 140 may be linked through a network 138 to external databases 156 which may also have records for this particular patient. In that event, the pharmacist computer 140 performs a similar search and comparison in those external databases 156. If this comparison reveals contraindications, the remote pharmacist follows the preestablished policy to address those concerns.

In addition in the exemplary embodiment the pharmacist's computer 140 compares the prescription to the customer's medical plan, contained in the rules database 152, to determine if generic substitutions are permitted, whether the medication prescribed is in the formulary for the patient's health plan, and any applicable co-pays. If any of these inquiries raise concerns, the remote pharmacist follows the preestablished policy to address those concerns.

Although in this exemplary embodiment, this second review is done after the prescription is filled, in other embodiments it may be done before the prescription is filled in order to avoid restocking prescriptions if, for example, the customer might choose not to fill a prescription for a medication that is not part if the insurance company's formulary, or might choose to purchase a generic substitute instead of a more expensive named product. Much of this verification may be automated in some embodiments, and can also occur while the prescription or order is being prepared.

Concluding the Transaction

Before delivering the medication or other item to the customer, the remote pharmacist may offer to counsel the customer about the item ordered, represented in a step 550 in FIG. 14. In this exemplary embodiment the pharmacist computer 140 is programmed to generate a limited list of concerns using the information acquired during the review process. The list of concerns might include drug interactions, allergies, side effects, or insurance questions. The remote pharmacist reviews the list, selects the concerns that should be shared with the customer, and electronically transmits those concerns over the network 138 to the patient. The concerns are displayed on the video monitor 174 or 276 to the customer, along with an offer to counsel the patient. If the customer wishes to speak with the remote pharmacist, an interactive consultation takes place via an audiovisual link through the CCTV located in customer terminals 103 or at the customer service area 102 to which the customer has access.

Although in this exemplary embodiment, the remote pharmacist uses the video monitor 174 or 276 to transmit concerns to the patient, the concerns could also be transmitted to the customer in printed format using one of the output devices at a customer terminal 103 or the customer service station 102. In addition, although the remote pharmacist may make counseling available to the customer immediately via CCTV, the remote pharmacist may also offer to provide counseling over the telephone after the customer has returned home and has had a chance to review any printed information he or she received. In that event, the remote pharmacist will provide a telephone number to the customer for his or her later use.

Following this consultation, the prescription is paid for and the product is delivered to the customer, represented in a step 560. In the exemplary embodiment at the customer terminal 103, the cost of the prescription may be displayed on the monitor. The customer may select a method of payment via the touch screen option. If the customer wishes to pay by a credit or a debit card, a customer may use the card reader at the customer terminal 103 and follow the automated procedure to authorize payment. Access to the credit or debit processing locations 120 and 118 is obtained through the pharmacy computer 114. In the alternative, if the customer wishes to pay by cash or check, the customer uses a carrier transmitted in the pneumatic delivery tube 139 to send the cash or a check to the technician in the customer service area 103. A pharmacy 100 may also use a check scanner, so that payment by check may be made by passing a check through a check scanner, which is connected to an electronic debit processing location 120 through the pharmacy computer 114.

If payment is made at the customer service area 102, the technician processes the payment by normal commercial means. In the exemplary embodiment once the payment has been processed, the drug delivery robot 262 is directed to deliver the prescription to the customer via the pneumatic delivery tube 274. The technician, or a remote pharmacist, directs a drug information sheet to be printed at the customer terminal 103 or the customer service area 102. In addition, the remote pharmacist directs any other information that must be provided to the customer to be printed at the customer terminal 103 or the customer service area 102. Although in this embodiment, the drug information sheet is printed at the pick-up location for the filled prescription, in other embodiments, the drug information sheet or other information may be printed in the drug retrieval vault 126, and sent to the customer through the pneumatic delivery tubes 129 or 134. In still other embodiments it may be provided to the customer in a format other than a printed page. For example, if the customer has the capability to read magnetically or electronically encoded information, the information may be encoded on a magnetic or smart card for the customer. Similarly, if the customer has access to the Internet, the remote pharmacist may provide the customer with an access code to an Internet site, having the information, rather than provide the information in printed form.

Although the procedures above are described as occurring in a particular order, the individual tasks may be performed in another order that is desirable for a particular pharmaceutical system 50 or pharmacy 100, as long as the tasks may logically be done in that order. For example, it may be desirable to perform all of the steps necessary to provide a price to the customer before the prescription or order is prepared, if prescriptions are frequently rejected in pharmacy 100 because of the cost. The steps may even be selectively performed out of order based on the nature of the item ordered. For example, it may be desirable for the remote pharmacist to survey both the resident databases 144, 148, 152 and external databases 156 when a customer orders a drug that is commonly sold illegally, in order to determine if this particular customer has ordered the medication recently from this or another pharmacy.

Many of the tasks assigned to the technician or the remote pharmacist are described as being done or performed by them. This description is intended to include the performance of tasks, or portions of tasks, by automated means which do not necessarily require the individual's conscious attention to the task. For example, the remote pharmacist is described as searching various databases during the second review of the prescription. This description is intended to include searches that are performed using preprogrammed routines, even those that may be automatically triggered when the pharmacist terminal 162 receives a transmitted prescription request. It is also intended to include manual searches of those same databases that are consciously undertaken and directly performed by the remote pharmacist.

Finally, the location of the remote pharmacist is not explicitly described because the remote pharmacist may work from any location which can support the electronic equipment required to perform the tasks described above. As suggested above, this site could be one of the pharmacies served. In the alternative, it could be the residence of the remote pharmacist, or it could be a central building from which several remote pharmacists serve. A group of pharmacies could also be served from more than one location, switching from service by one location to service by another from time to time. The location of the remote pharmacist is relatively unlimited, aside from the requirement that the location be electronically accessible and capable of supporting a computer, databases, phone lines, CCTV, and any other electronics necessary to perform the tasks above.

Thus the exemplary method of pharmacy automation achieves the above stated objectives, eliminates difficulties encountered in the use of prior methods, solves problems and attains the desirable results described herein.

In the foregoing description certain terms have been used for brevity, clarity, and understanding, however no unnecessary limitations are to be implied therefrom because such terms are used for descriptive purposes and are intended to be broadly construed. Moreover, the descriptions and illustrations herein are by way of examples and the invention is not limited to the exact details shown and described.

In the following claims any feature described as a means for performing a function shall be construed as encompassing any means known to those skilled in the art to be capable of performing the recited function and shall not be limited to the structures shown herein or mere equivalents thereof.

Having described the features, discoveries and the principles of the invention, the manner in which it is constructed and operated and the advantages and useful results attained; the new and useful structures, device elements, arrangements, parts, combinations, systems, equipment, operations, methods and relationships are set forth in the appended claims.

I claim:

1. A method comprising:
   (a) receiving a prescription at a pharmacy;
   (b) transmitting data corresponding to the prescription electronically to a pharmacist located remotely from the pharmacy;
   (c) preparing a medical item corresponding to the prescription at the pharmacy responsive to direction received electronically from the pharmacist;
   (d) delivering the medical item corresponding to the prescription to a customer.

2. The method according to claim 1 wherein step (a) includes providing at least one input through a keypad on a customer terminal.

3. The method according to claim 1 wherein step (a) comprises reading machine readable indicia with a reading device.

4. The method according to claim 1 and further comprising conferring with the customer by the pharmacist via an audio visual link.

5. The method according to claim 1 and further comprising generating through operation of a computer a plurality of concerns related to the medical item and transmitting at least one of the concerns to the customer.

6. The method according to claim 1 and further comprising:
   (e) receiving a further prescription at a further pharmacy;
   (f) transmitting data corresponding to the further prescription electronically to the pharmacist;
   (g) preparing a further medical item corresponding to the further prescription at the further pharmacy responsive to direction received electronically from the pharmacist;
   (h) delivering the further medical item corresponding to the further prescription to a further customer.

7. The method according to claim 1 wherein (c) is subsequent to (b), and wherein (b) is subsequent to (a).

8. The method according to claim 1 wherein step (a) comprises receiving the prescription in a form including audio, and wherein step (b) comprises transmitting data corresponding to the audio to the pharmacist.

9. The method according to claim 8 and further comprising converting the audio to corresponding text, and prior to step (d) comparing the audio and text by the pharmacist.

10. The method according to claim 1 wherein step (a) comprises producing an electronic representation of the prescription through operation of a scanner.

11. The method according to claim 10 and further comprising subsequent to step (a) and prior to step (d), transcribing data from the prescription at the pharmacy, and wherein in step (b) both the electronic representation of the prescription and the transcribed data are transmitted to the pharmacist.

12. The method according to claim 11 and prior to step (d) comparing by the pharmacist of the electronic representation of the prescription and the transcribed data.

13. The method according to claim 1 wherein step (c) comprises controlling at least one robot in the pharmacy by the pharmacist.

14. The method according to claim 13 wherein step (c) comprises the pharmacist controlling a drug retrieval robot and a compounding robot in the pharmacy.

15. The method according to claim 14 and further comprising in step (c) transporting constituent items between the drug retrieval robot and the compounding robot.

16. The method according to claim 15 wherein in step (c) comprises transporting the constituent items through a pneumatic tube system.

17. The method according to claim 13 wherein step (c) comprises operating the at least one robot to select and measure a quantity of a constituent item.

18. The method according to claim 14 wherein step (c) comprises operation of the drug retrieval robot to select a plurality of constituent items, and operating the compounding robot to mix the plurality of constituent items to produce a compound item.

19. The method according to claim 18 wherein step (c) further comprises transporting at least one of the plurality of constituent items between the drug retrieval robot and the compounding robot through a pneumatic tube system.

20. The method according to claim 19 wherein step (c) further comprises transporting the compound item through the pneumatic tube system to the drug retrieval robot and storing the compound item through operation of the drug retrieval robot.

21. The method according to claim 20 wherein step (c) further comprises labeling the compound item through operation of the drug retrieval robot.

22. The method according to claim 21 and prior to step (d) further comprising viewing of the labeled compound item through operation of a camera in the pharmacy.

23. The method according to claim 1 wherein step (c) comprises labeling the medical item prior to step (d).

24. The method according to claim 23 and prior to step (d) further comprising viewing of the labeled medical item by the pharmacist through operation of a camera in the pharmacy.

25. The method according to claim 24 and prior to step (d) further comprising receiving payment from the customer for the medical item.

26. The method according to claim 25 and further comprising conferring with the customer by the pharmacist via an audio visual link.

27. The method according to claim 25 and further comprising generating through operation of a computer a plurality of concerns related to the medical item and transmitting at least one of the concerns to the customer.

28. The method according to claim 25 wherein step (d) comprises delivering the medical item to the customer through a pneumatic tube system.

29. The method according to claim 25 and prior to step (d) further comprising checking at least one online database by the pharmacist which database contains information pertinent to at least one of the customer and the medical item.

30. The method according to claim 29 wherein the checking step includes checking at least one online database that includes data corresponding to medications prescribed for the customer.

31. The method according to claim 29 wherein the checking step comprises checking at least one online database including information concerning a medical insurance plan associated with the customer.

32. A method comprising:
   (a) transferring a prescription from a store customer to a pharmacy within a
   (b) filling the prescription at the pharmacy using at least one medical item preparing action controlled electronically by a pharmacist remotely located from the pharmacy, wherein the filling results in at least one medical item;
   (c) transferring the at least one medical item from the pharmacy to a store customer.

33. A method comprising:
   (a) receiving a first prescription from a first customer at a first pharmacy;
   (b) filling the first prescription at the first pharmacy, wherein the filling includes at least one medical item preparing action controlled electronically by a pharmacist remotely located from the first pharmacy, wherein the filling results in a first medical item deliverable to the first customer;
   (c) receiving a second prescription from a second customer at a second pharmacy remotely located from the first pharmacy;
   (d) filling the second prescription at the second pharmacy responsive to at least one medical item preparing action by the pharmacist, wherein the filling results in a second medical item deliverable to the second customer.

* * * * *

UNITED STATES PATENT AND TRADEMARK OFFICE
CERTIFICATE OF CORRECTION

PATENT NO. : 6,711,460 B1 Page 1 of 1
DATED : March 23, 2004
INVENTOR(S) : Rod Reese It is certified that error appears in the above-identified patent and that said Letters Patent is hereby corrected as shown below:

Column 25,
Line 20, after "within a" insert -- store --.

Signed and Sealed this

Twenty-fifth Day of May, 2004

JON W. DUDAS
*Acting Director of the United States Patent and Trademark Office*